United States Patent
Libbus et al.

(10) Patent No.: US 11,612,749 B2
(45) Date of Patent: Mar. 28, 2023

(54) VAGUS NERVE STIMULATION PATIENT SELECTION

(71) Applicant: LivaNova USA, Inc., Houston, TX (US)

(72) Inventors: Imad Libbus, St. Paul, MN (US); Bruce H. Kenknight, Maple Grove, MN (US); Christine Henry, Clamart (FR)

(73) Assignee: LivaNova USA, Inc., Houston, TX (US)

( * ) Notice: Subject to any disclaimer, the term of this patent is extended or adjusted under 35 U.S.C. 154(b) by 187 days.

(21) Appl. No.: 16/090,088

(22) PCT Filed: Mar. 31, 2017

(86) PCT No.: PCT/US2017/025476
§ 371 (c)(1),
(2) Date: Sep. 28, 2018

(87) PCT Pub. No.: WO2017/173331
PCT Pub. Date: Oct. 5, 2017

(65) Prior Publication Data
US 2020/0254259 A1 Aug. 13, 2020

Related U.S. Application Data

(60) Provisional application No. 62/318,156, filed on Apr. 4, 2016, provisional application No. 62/317,352, filed on Apr. 1, 2016.

(51) Int. Cl.
*A61N 1/36* (2006.01)
*A61N 1/05* (2006.01)
*A61N 1/372* (2006.01)

(52) U.S. Cl.
CPC ......... *A61N 1/36135* (2013.01); *A61N 1/056* (2013.01); *A61N 1/0556* (2013.01);
(Continued)

(58) Field of Classification Search
CPC .. A61N 1/36053; A61N 1/36114; A61N 1/05; A61N 1/0551; A61N 1/0558;
(Continued)

(56) References Cited

U.S. PATENT DOCUMENTS 5,792,187 A 8/1998 Adams
6,429,217 B1 8/2002 Puskas
(Continued)

FOREIGN PATENT DOCUMENTS

JP 2008-522725 A 7/2008
JP 2010-502271 1/2010
(Continued)

OTHER PUBLICATIONS

Ahmad, Tariq, et al. "Clinical implications of chronic heart failure phenotypes defined by cluster analysis." Journal of the American College of Cardiology 64.17 (2014): 1765-1774.
(Continued)

*Primary Examiner* — Jon Eric C Morales
(74) *Attorney, Agent, or Firm* — Foley & Lardner LLP

(57) ABSTRACT

A method for assessing a patient's suitability for receiving a vagus nerve stimulation therapy includes receiving a criterion regarding the patient's suitability for receiving a vagus nerve stimulation therapy; controlling a stimulation device to provide stimulation to a vagus nerve of the patient; receiving, from a sensor, response data indicative of a physiological response of the patient to the stimulation of the vagus nerve; and determining the patient's suitability for
(Continued)

receiving the vagus nerve stimulation therapy based on the criterion and the physiological response of the patient to the stimulation.

20 Claims, 8 Drawing Sheets

(52) U.S. Cl.
CPC ...... *A61N 1/36036* (2017.08); *A61N 1/36114* (2013.01); *A61N 1/37247* (2013.01)

(58) Field of Classification Search
CPC .... A61N 1/056; A61N 1/057; A61N 1/36064; A61N 1/36085; A61N 1/36125; A61N 1/36128; A61N 1/36135; A61N 2001/0585; A61B 2562/0209; A61B 5/024; A61B 5/0402; A61B 5/048; A61B 5/4094; A61B 5/4848; A61B 5/686; A61B 5/7203; A61B 5/7285; A61M 25/09
See application file for complete search history.

(56) References Cited

U.S. PATENT DOCUMENTS

| | | | |
|---|---|---|---|
| 6,479,523 B1 | 11/2002 | Puskas | |
| 6,778,854 B2 | 8/2004 | Puskas | |
| 6,934,583 B2 | 8/2005 | Weinberg et al. | |
| 7,072,720 B2 | 7/2006 | Puskas | |
| 7,082,336 B2 | 7/2006 | Ransbury et al. | |
| 7,142,910 B2 | 11/2006 | Puskas | |
| 7,184,829 B2 | 2/2007 | Hill et al. | |
| 7,225,019 B2 | 5/2007 | Jahns et al. | |
| 7,231,260 B2 | 6/2007 | Wallace et al. | |
| 7,310,552 B2 | 12/2007 | Puskas | |
| 7,529,589 B2 | 5/2009 | Williams et al. | |
| 7,840,278 B1 | 11/2010 | Puskas | |
| 7,917,230 B2 | 3/2011 | Bly | |
| 7,925,352 B2 | 4/2011 | Stack et al. | |
| 7,949,409 B2 | 5/2011 | Bly et al. | |
| 8,116,883 B2 | 2/2012 | Williams et al. | |
| 8,239,045 B2 | 8/2012 | Ransbury et al. | |
| 8,244,378 B2 | 8/2012 | Bly et al. | |
| 8,311,647 B2 | 11/2012 | Bly | |
| 8,369,954 B2 | 2/2013 | Stack et al. | |
| 8,412,350 B2 | 4/2013 | Bly | |
| 8,504,161 B1 | 8/2013 | Kornet et al. | |
| 8,532,793 B2 | 9/2013 | Morris et al. | |
| 8,571,662 B2 | 10/2013 | Hoffer | |
| 8,594,797 B2 | 11/2013 | Lee | |
| 8,612,019 B2 | 12/2013 | Moffitt | |
| 8,812,124 B2 | 8/2014 | Lee | |
| 8,868,196 B2 | 10/2014 | Lee et al. | |
| 9,026,231 B2 | 5/2015 | Hoffer | |
| 9,050,453 B2 | 6/2015 | Inagaki et al. | |
| 9,061,154 B2 | 6/2015 | Parker et al. | |
| 9,108,058 B2 | 8/2015 | Hoffer | |
| 9,108,059 B2 | 8/2015 | Hoffer | |
| 9,168,377 B2 | 10/2015 | Hoffer | |
| 9,220,898 B2 | 12/2015 | Hoffer | |
| 2003/0078623 A1* | 4/2003 | Weinberg | A61N 1/056 607/9 |
| 2005/0080462 A1* | 4/2005 | Jenkins | G16H 20/10 607/58 |
| 2006/0122675 A1 | 6/2006 | Libbus et al. | |
| 2007/0150024 A1 | 6/2007 | Leyde et al. | |
| 2008/0132964 A1 | 6/2008 | Cohen et al. | |
| 2008/0208266 A1 | 8/2008 | Lesser et al. | |
| 2008/0300645 A1 | 12/2008 | Cholette | |
| 2009/0125076 A1 | 5/2009 | Shuros et al. | |
| 2009/0228078 A1 | 9/2009 | Zhang et al. | |
| 2009/0276025 A1* | 11/2009 | Burnes | A61N 1/36053 607/126 |
| 2010/0114227 A1* | 5/2010 | Cholette | A61N 1/3621 607/17 |
| 2010/0131026 A1 | 5/2010 | Pastore et al. | |
| 2010/0286553 A1 | 11/2010 | Feler et al. | |
| 2012/0172680 A1 | 7/2012 | Gelfand et al. | |
| 2012/0239116 A1 | 9/2012 | Lee et al. | |
| 2013/0006332 A1 | 1/2013 | Sommer et al. | |
| 2013/0138173 A1 | 5/2013 | Bianchi et al. | |
| 2013/0238047 A1 | 9/2013 | Libbus et al. | |
| 2014/0275827 A1 | 9/2014 | Gill et al. | |
| 2014/0277232 A1 | 9/2014 | Libbus et al. | |
| 2014/0288617 A1 | 9/2014 | Rosellini | |
| 2014/0316487 A1 | 10/2014 | Libbus et al. | |
| 2014/0324118 A1 | 10/2014 | Simon et al. | |
| 2015/0005847 A1 | 1/2015 | Lee | |
| 2015/0241447 A1 | 8/2015 | Zitnik et al. | |
| 2016/0045745 A1 | 2/2016 | Mathur et al. | |
| 2016/0310070 A1* | 10/2016 | Sabesan | A61B 5/024 |

FOREIGN PATENT DOCUMENTS

| | | |
|---|---|---|
| WO | WO-2008/027233 A1 | 3/2008 |
| WO | WO-2011/005607 A1 | 1/2011 |

OTHER PUBLICATIONS

Alter, Peter, et al. "Airflow limitation in COPD is associated with increased left ventricular wall stress in coincident heart failure." Respiratory medicine 109.9 (2015): 1131-1137.
Anastasiou-Nana, Maria I., et al. "Prognostic value of iodine-123-metaiodobenzylguanidine myocardial uptake and heart rate variability in chronic congestive heart failure secondary to ischemic or idiopathic dilated cardiomyopathy." The American Journal of Cardiology 96.3 (2005): 427-431.
Babick, Andrea, et al. "Reversal of cardiac dysfunction and subcellular alterations by metoprolol in heart failure due to myocardial infarction." Journal of cellular physiology 228.10 (2013): 2063-2070.
Battipaglia, Irma, et al. "Relationship between cardiac autonomic function and sustained ventricular tachyarrhythmias in patients with an implantable cardioverter defibrillators." Europace 12.12 (2010): 1725-1731.
Bauer, Axel, et al. "Deceleration capacity of heart rate as a predictor of mortality after myocardial infarction: cohort study." The lancet 367.9523 (2006): 1674-1681.
Bibevski, Steve, et al. "Evidence for impaired vagus nerve activity in heart failure." Heart failure reviews 16.2 (2011): 129-135.
Bilchick, Kenneth C., et al. "Prognostic value of heart rate variability in chronic congestive heart failure (Veterans Affairs' Survival Trial of Antiarrhythmic Therapy in Congestive Heart Failure)." The American Journal of Cardiology 90.1 (2002): 24-28.
BioControl Medical. (2015). INOVATE-HF study closure [Press release]. Retrieved from http://www.biocontrol-medical.com/press_item.php?ID=29. 1 page.
BioControl Medical. INcrease Of VAgal TonE in CHF (INOVATE-HF)—A Randomized Study to Establish the Safety and Efficacy of CardioFit® for the Treatment of Subjects With Heart Failure and Left Ventricular Dysfunction. In: ClinicalTrials.gov [Internet]. Bethesda (MD): National Library of Medicine (US). (2011) [last updated Dec. 11, 2015] [cited Mar. 29, 2016]. Available from: https://clinicaltrials.gov/ct2/show/NCT01303718 NLM Identifier: NCT01303718. 4 pages.
Boscokovic, Aneta, et al. "Prognostic value of heart rate variability in post-infarction patients." Vojnosanitetski pregled 71.10 (2014): 925-930.
Boveda, Serge, et al. "Prognostic value of heart rate variability in time domain analysis in congestive heart failure." Journal of interventional cardiac electrophysiology 5.2 (2001): 181-187.
Bristow, Michael R. "The adrenergic nervous system in heart failure." (1984): 850-851.
Brunet-Bernard, Anne, et al. "Combined score using clinical, electrocardiographic, and echocardiographic parameters to predict left ventricular remodeling in patients having had cardiac resynchronization therapy six months earlier." The American journal of cardiology 113.12 (2014): 2045-2051.

(56) References Cited

OTHER PUBLICATIONS

Canbay, Alper, et al. "Procalcitonin: a marker of heart failure." Acta cardiologica 70.4 (2015): 473-478.
Cao, Thong Huy, et al. "Identification of novel biomarkers in plasma for prediction of treatment response in patients with heart failure." The Lancet 385 (2015): S26. 1 page.
Cha, Yong-Mei, et al. "Cardiac resynchronization therapy upregulates cardiac autonomic control." Journal of Cardiovascular Electrophysiology 19.10 (2008): 1045-1052.
Colucci, Wilson S. "The effects of norepinephrine on myocardial biology: implications for the therapy of heart failure." Clinical cardiology 21.S1 (1998): 20-24.
Davoodi, Gholamreza, et al. "Evaluation of In-Hospital NT-proBNP Changes in Heart Failure Patients to Identify the Six-Month Clinical Response Following Cardiac Resynchronization Therapy." Acta Medica Iranica 52.1 (2014): 15-23. 9 pages.
Dzau, Victor J., et al. "Relation of the renin-angiotensin-aldosterone system to clinical state in congestive heart failure." Circulation 63.3 (1981): 645-651.
Esler, Murray, et al. "Adrenergic nervous system in heart failure." The American journal of cardiology 80.11 (1997): 7L-14L.
Fauchier, Laurent, et al. "Prognostic value of heart rate variability for sudden death and major arrhythmic events in patients with idiopathic dilated cardiomyopathy." Journal of the American College of Cardiology 33.5 (1999): 1203-1207.
Florea, Viorel G., et al. "The autonomic nervous system and heart failure." Circulation research 114.11 (2014): 1815-1826.
Frenneaux, M. P. "Autonomic changes in patients with heart failure and in post-myocardial infarction patients." Heart 90.11 (2004): 1248-1255.
Galinier, M., et al. "Depressed low frequency power of heart rate variability as an independent predictor of sudden death in chronic heart failure." European heart journal 21.6 (2000): 475-482.
Germany, Robin. "The Use of Device-Based Diagnostics to Manage Patients With Heart Failure." Congestive Heart Failure 14.s2 (2008): 19-24.
Gold, Michael R. et al., "The Effect of Vagal Nerve Stimulation in Heart Failure: Primary Results of the INcrease Of VAgal TonE in chronic Heart Failure (INOVATE-HF) Trial" [PowerPoint], Late-Breaking Clinical Trials: Deep Dive II, Session 415-08, ACC.16 Scientific Session, American College of Cardiology, Apr. 4, 2016, Chicago, IL. 12 pages.
Gold, Michael R. "The Effect of Vagal Nerve Stimulation in Heart Failure: Primary Results of the INcrease Of VAgal TonE in chronic Heart Failure (INOVATE-HF) Trial" [Transcript], Late-Breaking Clinical Trials: Deep Dive II, Session 415-08, ACC.16 Scientific Session, American College of Cardiology, Apr. 4, 2016, Chicago, IL. 2 pages.
Gold, Michael R. et al., "The Effect of Vagal Nerve Stimulation in Heart Failure: Primary Results of the INcrease Of VAgal TonE in chronic Heart Failure (INOVATE-HF) Trial" [Abstract], Late-Breaking Clinical Trials, Session 412-12, ACC.16 Scientific Session, American College of Cardiology, Apr. 4, 2016, Chicago, IL. 1 page.
Gold, Michael R. et al., "The Effect of Vagal Nerve Stimulation in Heart Failure: Primary Results of the INcrease Of VAgal TonE in chronic Heart Failure (INOVATE-HF) Trial" [PowerPoint], Late-Breaking Clinical Trials, Session 412-12, ACC.16 Scientific Session, American College of Cardiology, Apr. 4, 2016, Chicago, IL. 18 pages.
Gold, Michael R. et al., "The Effect of Vagal Nerve Stimulation in Heart Failure: Primary Results of the INcrease Of VAgal TonE in chronic Heart Failure (INOVATE-HF) Trial" [Transcript], Late-Breaking Clinical Trials, Session 412-12, ACC.16 Scientific Session, American College of Cardiology, Apr. 4, 2016, Chicago, IL. 3 pages.
Gold, Michael R., et al. "Vagus nerve stimulation for the treatment of heart failure: The INOVATE-HF trial." Journal of the American College of Cardiology 68.2 (2016): 149-158.
Guzzetti, S., et al. "Sympathetic predominance followed by functional denervation in the progression of chronic heart failure." European heart journal 16.8 (1995): 1100-1107.
Guzzetti, Stefano, et al. "Different spectral components of 24 h heart rate variability are related to different modes of death in chronic heart failure." European Heart Journal 26.4 (2005): 357-362.
Hoffmann, J., et al. "Heart rate variability and baroreflex sensitivity in idiopathic dilated cardiomyopathy." Heart 83.5 (2000): 531-536.
International Search Report and Written Opinion for International Application No. PCT/US2017/25476 dated Aug. 24, 2017, 19 pages.
Jacobson, Arnold F., et al. "$^{123}$I-mIBG scintigraphy to predict risk for adverse cardiac outcomes in heart failure patients: Design of two prospective multicenter international trials." Journal of nuclear cardiology 16.1 (2009): 113-121.
Kaul, Sanjay, Armstrong, Paul W., et al. "Panel Discussion re: The Effect of Vagal Nerve Stimulation in Heart Failure: Primary Results of the INcrease Of VAgal TonE in chronic Heart Failure (INOVATE-HF) Trial" [Transcript], Late-Breaking Clinical Trials: Deep Dive II, Session 415-10, ACC.16 Scientific Session, American College of Cardiology, Apr. 4, 2016, Chicago, IL. 3 pages.
Kleiger, Robert E., et al. "Decreased heart rate variability and its association with increased mortality after acute myocardial infarction." The American journal of cardiology 59.4 (1987): 256-262.
Kuch et al. "Extent of the Decrease of 28-Day Case Fatality of Hospitalized Patients With Acute Myocardial Infarction Over 22 Years. Epidemiological Versus Clinical View: The MONICA/KORA Augsburg Infarction Registry". Circ Cardiovasc Qual Outcomes. 2009;2:313-319. 7 pages.
La Rovere, Maria Teresa, et al. "Baroreflex sensitivity and heart-rate variability in prediction of total cardiac mortality after myocardial infarction." The Lancet 351.9101 (1998): 478-484.
La Rovere, Maria Teresa, et al. "Prognostic implications of baroreflex sensitivity in heart failure patients in the beta-blocking era." Journal of the American College of Cardiology 53.2 (2009): 193-199.
La Rovere, Maria Teresa, et al. "Short-term heart rate variability strongly predicts sudden cardiac death in chronic heart failure patients." Circulation 107.4 (2013): 565-570.
Lahiri, Marc K., et al. "Assessment of autonomic function in cardiovascular disease." Journal of the American College of Cardiology 51.18 (2008): 1725-1733.
Lambert, Elisabeth, et al. "Differing pattern of sympathoexcitation in normal-weight and obesity-related hypertension." Hypertension 50.5 (2007): 862-868.
Liang, Chang-seng, et al. "Alterations by norepinephrine of cardiac sympathetic nerve terminal function and myocardial β-adrenergic receptor sensitivity in the ferret." Circulation 102.1 (2000): 96-103.
Lymperopoulos, Anastasios, "The adrenergic nervous system in heart failure." Circulation research 113.6 (2013): 739-753.
Moore, R., et al. "Altered short term heart rate variability with spinal cord stimulation in chronic refractory angina: evidence for the presence of procedure related cardiac sympathetic blockade." Heart 90.2 (2004): 211-212.
Mortara, A., et al. "Can power spectral analysis of heart rate variability identify a high risk subgroup of congestive heart failure patients with excessive sympathetic activation? A pilot study before and after heart transplantation." British heart journal 71.5 (1994): 422-430.
Mortara, Andrea, et al. "Baroreceptor activation therapy: The importance of targeting the right patient: who needs to be treated?" European journal of heart failure 17.10 (2015): 1000-1002.
Murad, Khalil, et al. "Exercise Training Improves Heart Rate Variability in Older Patients With Heart Failure: A Randomized, Controlled, Single-Blinded Trial." Congestive Heart Failure 18.4 (2012): 192-197.
Myers, Jonathan, et al. "Effects of exercise training on heart rate recovery in patients with chronic heart failure." American Heart Journal 153.6 (2007): 1056-1063.
Nolan, James, et al. "Prospective study of heart rate variability and mortality in chronic heart failure." Circulation 98.15 (1998): 1510-1516.

(56) References Cited

OTHER PUBLICATIONS

Packer, Milton. "The neurohormonal hypothesis: A theory to explain the mechanism of disease progression in heart failure." Journal of the American College of Cardiology 20.1 (1992): 248-254.
Padeletti, Luigi, et al. "Metabolomic does not predict response to cardiac resynchronization therapy in patients with heart failure." Journal of Cardiovascular Medicine 15.4 (2014): 295-300.
Paratt, Gianfranco, et al. "The human sympathetic nervous system: its relevance in hypertension and heart failure." European heart journal (2012): 33 (9): 1058-1066.
Pepper, Gregory S., et al. "Sympathetic activation in heart failure and its treatment with β-blockade." Archives of Internal Medicine 159.3 (1999): 225-234.
Pinto, Fausto J., Walsh, Mary N., et al. "Panel Discussion re: The Effect of Vagal Nerve Stimulation in Heart Failure: Primary Results of the INcrease Of VAgal TonE in chronic Heart Failure (INOVATE-HF) Trial" [Transcript], Late-Breaking Clinical Trials, Session 412-13, ACC.16 Scientific Session, American College of Cardiology, Apr. 4, 2016, Chicago, IL. 3 pages.
Ponikowski, Piotr, et al. "Depressed heart rate variability as an independent predictor of death in chronic congestive heart failure secondary to ischemic or idiopathic dilated cardiomyopathy." The American journal of cardiology 79.12 (1997): 1645-1650.
Proclemer, A., et al. "The pacemaker and implantable cardioverter-defibrillator registry of the Italian Association Arrhythmology Cardiac Pacing and cardiac pacing-annual report 2013." Giornale italiano di cardiologia (2006) 15.11 (2014): 638-650.
Rona, G. "Catecholamine cardiotoxicity." J Mol Cell Cardiol, 17 (1985): 291-306.
Rydlewska, Agnieszka, et al. "Changes in autonomic balance in patients with decompensated chronic heart failure." Clinical Autonomic Research 21.1 (2011): 47-54.
Schmitz, Boris, et al. "Identification of genetic markers for treatment success in heart failure patients: Insight from cardiac resynchronization therapy." Circulation: Cardiovascular Genetics (2014): CIRCGENETICS-113.
Selig, Steve E., et al. "Moderate-intensity resistance exercise training in patients with chronic heart failure improves strength, endurance, heart rate variability, and forearm blood flow." Journal of Cardiac Failure 10.1 (2004): 21-30.
Singh, Jagmeet P., et al. "Non-pharmacological modulation of the autonomic tone to treat heart failure." European heart journal 35.2 (2014): 77-85.
Slart, Riemer H.J.A, Elsinga, Philip H., Tio, Rene A., & Schwaiger, Markus (Ed.). (2015). Autonomic innervation of the heart: Role of molecular imaging. Germany: Springer. 4 pages.
Ten Sande, Judith N., et al. "Value of serial heart rate variability measurement for prediction of appropriate ICD discharge in patients with heart failure." Journal of cardiovascular electrophysiology 25.1 (2014): 60-65.
Tereshchenko, Larisa G., et al. "Predictive Value of Beat-to-Beat QT Variability Index across the Continuum of Left Ventricular Dysfunction: Competing Risks of Non-Cardiac or Cardiovascular Death, and Sudden or Non-Sudden Cardiac Death." Circulation. Arrhythmia and Electrophysiology 5.4 (2012): 719-727.

Triposkiadis, Filippos, et al. "The sympathetic nervous system in heart failure: Physiology, pathophysiology, and clinical implications." Journal of the American College of Cardiology 54.19 (2009): 1747-1762.
Van De Borne, Philippe, et al. "Absence of low-frequency variability of sympathetic nerve activity in severe heart failure." Circulation 95.6 (1997): 1449-1454.
Vanoli, Emilio, et al. "Prediction of unexpected sudden death among healthy dogs by a novel marker of autonomic neural activity." Heart Rhythm 5.2 (2008): 300-305.
Watson, A. M. D., et al. "Mechanisms of sympathetic activation in heart failure." Clinical and experimental pharmacology and physiology 33.12 (2006): 1269-1274.
Watson, A. M. D, et al. "Increased cardiac sympathetic nerve activity in heart failure is not due to desensitization of the arterial baroreflex." American Journal of Physiology-Heart and Circulatory Physiology 293.1 (2007): H798-H804.
Wilson, John R., et al. "Exercise intolerance in patients with chronic heart failure: role of impaired nutritive flow to skeletal muscle." Circulation 69.6 (1984): 1079-1087.
Wustmann, Kerstin, et al. "Effects of chronic baroreceptor stimulation on the autonomic cardiovascular regulation in patients with drug-resistant arterial hypertension." Hypertension 54.3 (2009): 530-536.
Yaylali, Yt, et al. "The effects of baseline heart rate recovery normality and exercise training protocol on heart rate recovery in patients with heart failure." The Anatolian Journal of Cardiology 15.9 (2015): 727-734.
Zile, Michael R., et al. "Baroreflex activation therapy for the treatment of heart failure with a reduced ejection fraction: safety and efficacy in patients with and without cardiac resynchronization therapy." European journal of heart failure 17.10 (2015): 1066-1074.
Zipes, Douglas P. "'Deep Dive' Critique of The Effect of Vagal Nerve Stimulation in Heart Failure: Primary Results of the INcrease Of VAgal TonE in chronic Heart Failure (INOVATE-HF) Trial" [PowerPoint], Late-Breaking Clinical Trials: Deep Dive II, Session 415-09, ACC.16 Scientific Session, American College of Cardiology, Apr. 4, 2016, Chicago, IL. 11 pages.
Zipes, Douglas P. "'Deep Dive' Critique of The Effect of Vagal Nerve Stimulation in Heart Failure: Primary Results of the INcrease Of VAgal TonE in chronic Heart Failure (INOVATE-HF) Trial" [Transcript], Late-Breaking Clinical Trials: Deep Dive II, Session 415-09, ACC.16 Scientific Session, American College of Cardiology, Apr. 4, 2016, Chicago, IL. 2 pages.
Extended European search report on EP 17776820.7 dated Nov. 28, 2019. 5 pages.
Office Action issued in JP Application No. 2019-502535 dated Feb. 10, 2021.
Examination Report issued on Australian application No. 2017240755 dated Oct. 14, 2021.
Office Action issued on Israeli application No. 262009 dated Sep. 5, 2021.
Office Action issued in CN 2017800326629 dated Jan. 24, 2022.
Office Action issued in JP 2019-502535 dated Dec. 16, 2021.
CN Office Action with Search Report on CN Appl. Ser. No. 201780032662.9 dated Sep. 30, 2022 (21 pages).

* cited by examiner

VAGUS NERVE STIMULATION PATIENT SELECTION

CROSS-REFERENCE TO RELATED PATENT APPLICATIONS

This application claims priority to and the benefit of U.S. Provisional Patent Application 62/317,352, filed Apr. 1, 2016 and U.S. Provisional Patent Application 62/318,156, filed Apr. 4, 2016, both of which are hereby incorporated by reference in their entireties.

BACKGROUND

Congestive heart failure (CHF) is a progressive and physically debilitating chronic condition in which the heart is unable to supply sufficient blood flow to meet the body's needs. Pathologically, CHF is characterized by an elevated neuroexitatory state accompanied by impaired arterial and cardiopulmonary baroreflex function and reduced vagal activity. CHF is initiated by cardiac dysfunction, which triggers compensatory activations of the sympathoadrenal (sympathetic) nervous and the renin-angiotensin-aldosterone hormonal systems. Initially, these mechanisms help the heart compensate for deteriorating pumping function, yet over time, overdriven sympathetic activation and increased heart rate promote progressive left ventricular dysfunction and deleterious remodeling.

Chronic cardiac dysfunction stems from an autonomic imbalance of the sympathetic and parasympathetic nervous systems that, if left untreated, leads to cardiac arrhythmogenesis, including bradycardia, progressively worsening cardiac function and eventual death. The current standard of care for managing chronic cardiac dysfunction mandates prescription of pharmacological agents, including diuretics, angiotensin-converting enzyme inhibitors, angiotensin receptor blockers, beta-blockers, and aldosterone antagonists, and dietary and lifestyle changes. However, the effectiveness of these measures is only palliative, not curative, and patients often suffer side effects and comorbidities due to disease progression, such as pulmonary edema, sleep apnea, and myocardial ischemia.

Cardiac resynchronization therapy (CRT) has recently become available to those chronic cardiac dysfunction patients with impaired systolic function. CRT restores synchronous heartbeat through coordinated bi-ventricular pacing that helps improve contractile cardiac performance. However, CRT only addresses systolic dysfunction and is limited to patients exhibiting a wide QRS complex (mechanical dyssynchrony) and reduced left ventricular ejection fraction.

Neural stimulation has been proposed as a complementary treatment for chronic cardiac dysfunction that directly addresses the underlying autonomic nervous system imbalance, rather than relieving symptoms or directly pacing heart muscle. Activity within and among elements of both sympathetic and parasympathetic nervous systems regulate cardiovascular function by exerting high resolution control over key biological processes mediated by ionic currents flowing across cell membranes. Cumulatively, in a healthy person, the autonomic regulation of these biological processes results in stable homeostasis of heart rate and normal contractile performance. However, when disease processes derange autonomic function, homeostasis is lost and cardiovascular function is degraded; contractile performance thus becomes suboptimal and heart rate modulation is distorted in ways that create a positive feedback loop that promotes progression of chronic cardiac dysfunction and ultimately risks CHF. Neural stimulation can break the positive feedback loop through the suppression of excessive neural activation by electrically modulating select vagus nerve fibers. The electrical modulation may help improve cardiac mechanical function and reduce the heart's intrinsic nervous system's propensity to induce atrial and ventricular arrhythmias, including bradycardia, during chronic autonomic nervous system imbalance.

Vagus nerve stimulation (VNS) is currently only approved for the clinical treatment of drug-refractory epilepsy and depression, although VNS has been proposed as a long-term therapeutic treatment of CHF. However, the efficacy of VNS may vary from patient to patient such that VNS may positively affect some patients, while minimally or even adversely affecting other patients.

SUMMARY

One embodiment relates to a method for assessing a patient's suitability for receiving a vagus nerve stimulation therapy. The method includes receiving a criterion regarding the patient's suitability for receiving a vagus nerve stimulation therapy; controlling a stimulation device to provide stimulation to a vagus nerve of the patient; receiving, from a sensor, response data indicative of a physiological response of the patient to the stimulation of the vagus nerve; and determining the patient's suitability for receiving the vagus nerve stimulation therapy based on the criterion and the physiological response of the patient to the stimulation.

Another embodiment relates to a method for assessing a patient's suitability for receiving a vagus nerve stimulation therapy. The method includes receiving a criterion regarding the patient's suitability for receiving a vagus nerve stimulation therapy; receiving a characteristic of the patient; and determining the patient's suitability for receiving the vagus nerve stimulation therapy based on the criterion and the characteristic of the patient.

Still another embodiment relates to a method for assessing a patient's suitability for receiving a vagus nerve stimulation therapy. The method includes receiving a criterion regarding a patient's suitability for receiving the vagus nerve stimulation therapy;

receiving a characteristic of the patient; determining a value for the characteristic based on the characteristics relative to the criterion; and determining the patient's suitability for receiving the vagus nerve stimulation therapy based on the value relative to an efficacy mapping, wherein the efficacy mapping includes a threshold.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

Figure 1:
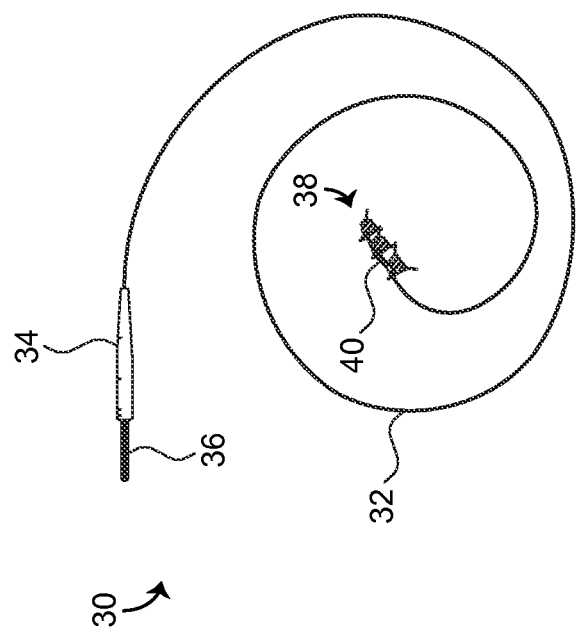
FIG. 1 is an illustration of a nerve stimulation device having a neurostimulator and a lead, according to an exemplary embodiment.
Figure 1:
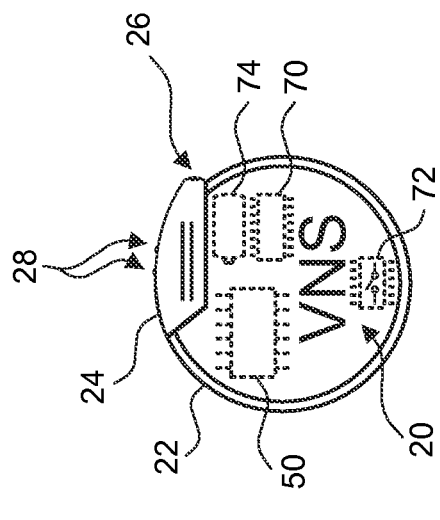

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

Referring to the Figures generally, the present disclosure relates to apparatuses, systems, and methods for identifying patients who are compatible and/or incompatible with the use of VNS to treat and/or reduce the likelihood of experiencing heart failure. Heart failure is a complex clinical syndrome having symptoms and signs that suggest impairment of the heart as a pump supporting physiological circulation which may be caused by structural and/or functional abnormalities of the heart. The prevalence of heart failure is widespread, affecting approximately 1-2% of the general population. Despite recent advances in therapeutic strategies, management of progressive heart failure continues to remain a significant challenge.

The pathophysiology of heart failure is characterized by hemodynamic abnormalities that result in neurohormonal activation and autonomic imbalance with increase in sympathetic activity of the sympathetic system and withdrawal of vagal activity of the parasympathetic system. The sympathetic system involves circulating hormones with a positive chronotropic effect (e.g., heart rate increase to maintain cardiac output, etc.) and a positive inotropic effect (e.g., cardiac contractility increase through noradrenergic stimulation, etc.). The increased activity (e.g., energetic cost, etc.) of the sympathetic system may lead to a higher risk of myocardial ischemia (e.g., since myocardial oxygen uptake is also increased, etc.) and/or ventricular arrhythmia. The increased heart rate may also act negatively on the ventricular filling time which may further expose the heart and/or other organs to ischemia.

VNS may be used for the treatment of heart failure, as it includes activating the parasympathetic system, in order to compensate for the over-activity of the sympathetic system. During VNS, stimulation may be directly and/or indirectly applied to the vagus nerve with a lead having an electrode powered by an implantable neurostimulator. By way of example, the electrode (e.g., a cuff-type electrode, a helical-type electrode, etc.) may be attached to the exterior of the vagus nerve (e.g., at the cervical level of the vagus nerve, etc.) to provide VNS directly to the vagus nerve. By way of another example, the lead (e.g., a stent, a pig-tail lead, a screw-lead, a preformed lead, etc.) may be endovascularly positioned within the venous system. Such an endovascular lead may have the electrode positioned to provide VNS transvascularly through the venous system (e.g., through the walls of the superior vena cava, the pulmonary artery, the azygos vein, etc.) to the vagus nerve. An endovascular approach for the delivery of VNS may be characterized as endovascular vagus nerve stimulation (eVNS). In this document, the term "eVNS" may be used interchangeably with the term "VNS" unless noted otherwise. With regard to some embodiments eVNS may be considered to be an alternative to VNS, and with regard to other embodiments eVNS may be considered to be a subset of VNS.

It is believed that some forms of VNS therapy may not satisfactorily treat and/or may not reduce the risk or effects of heart failure for some patients, may deliver ineffective therapy to some patients, and/or may expose some patients to side effects or other risks. In particular, BioControl Medical in the INOVATE-HF study (ClinicalTrials.gov Identifier: NCT01303718) evaluated the long-term safety and efficacy of a vagus nerve stimulation system named the CardioFit® system but was reported to have stopped the study "due to statistical futility in the primary efficacy endpoint." It is believed that such negative outcomes may be mitigated or avoided if patients can be sufficiently screened and/or tested for certain characteristics and/or response parameters indicative as to whether the patient is an appropriate candidate to receive a VNS therapy. It is further believed that proper patient selection is a factor in the success of autonomic regulation therapy (ART) and/or VNS therapy.

According to an exemplary embodiment, the apparatuses, systems, and methods of the present disclosure may be used to identify patients that are suitable or unsuitable candidates for a VNS therapy supplied via a VNS and/or an eVNS device and/or method. Such may be done by determining which patients may respond well to VNS and/or eVNS, and which may not, thereby increasing the efficacy of the treatment. In one embodiment, the determination is based on one or more physiological characteristics of the patient (e.g., age, resting heart rate, heart rate variability, etc.). In other embodiments, the determination is based on a physiological response of the patient during an evaluation using a VNS and/or eVNS device and/or method to evaluate the patient. In yet other embodiments, the determination is based on a physiological response of the patient during an evaluation using an externally applied stimulation (e.g., to the ear, the chest, to the back, the neck, auricular VNS, etc.). In some embodiments, the determination is based on a combination of the one or more physiological characteristics, the physiological response during an evaluation using eVNS, the physiological response during an evaluation using VNS, and/or the physiological response during an evaluation using external stimulation. Such a determination may reduce unnecessary, invasive medical procedures from being performed to implant VNS neurostimulators in patients that may show indications of not responding to eVNS and/or VNS, thereby preventing adverse medical effects and/or unnecessary medical costs that may result from such procedures, as well as increasing the efficacy of ART via eVNS and/or VNS in heart failure. In particular embodiments, the preliminary evaluation of a patient with a non-invasive or minimally-invasive VNS and/or eVNS device and/or method is used to screen the patient and/or to generate information relevant to determine whether the patient can or should receive a more invasive procedure and/or an implanted VNS device and/or system.

Referring now to FIGS. 1-4B, a stimulation device, shown as vagus nerve stimulator 10, may be implanted within a person, shown as patient 100, or positioned externally relative to the body of the patient 100 to provide at least one of eVNS and VNS to a vagus nerve of the patient 100. According to the exemplary embodiments shown in FIGS. 1-4B, the vagus nerve stimulator 10 may provide such stimulation via a lead that terminates with an electrode. In some embodiments, the electrode is positioned on the vagus nerve of the patient. In some embodiments, the electrode is positioned near a portion of the vagus nerve to deliver the stimulation from a blood vessel proximate the vagus nerve. In some embodiments, the electrode is positioned outside of the body of the patient 100 on a peripheral nerve of the patient 100 that communicates with the vagus nerve, with the stimulation energy delivered through the skin of the patient 100 near, for example, the ear. The vagus nerve stimulator 10 may be adapted for use in managing chronic cardiac dysfunction through therapeutic bi-directional vagal stimulation. According to an exemplary embodiment, the vagus nerve stimulator 10 operates under several mechanisms of action. These mechanisms may include increasing parasympathetic outflow and inhibiting sympathetic effects by blocking norepinephrine release through stimulation. More importantly, the stimulation provided by the vagus nerve stimulator 10 may trigger the release of acetylcholine (ACh) into the synaptic cleft, which may have beneficial anti-arrhythmic, anti-apoptotic, and ectopy-reducing anti-inflammatory effects. As can be appreciated in the embodiments described below, it is to be understood that the embodiments presenting the vagus nerve stimulator 10 as an internal vagus nerve stimulator may be modified to substitute the internal vagus nerve stimulator delivering a stimulation energy to an electrode with an external vagus nerve stimulator delivering the stimulation energy to the electrode, and vice versa.

Figure 3A:
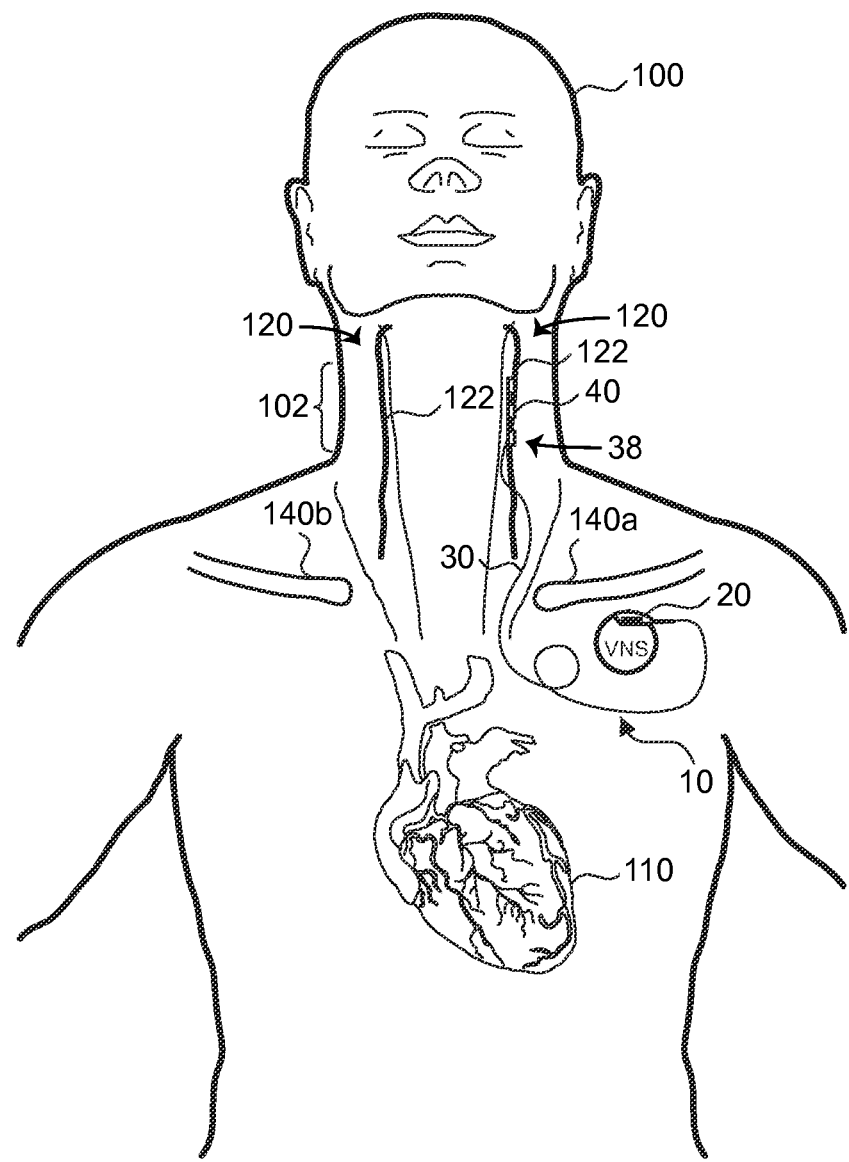
FIG. 3A is an illustration of the nerve stimulation device of FIG. 1 implanted within a patient to provide vagus nerve stimulation directly to the vagus nerve, according to an exemplary embodiment.
Figure 3B:
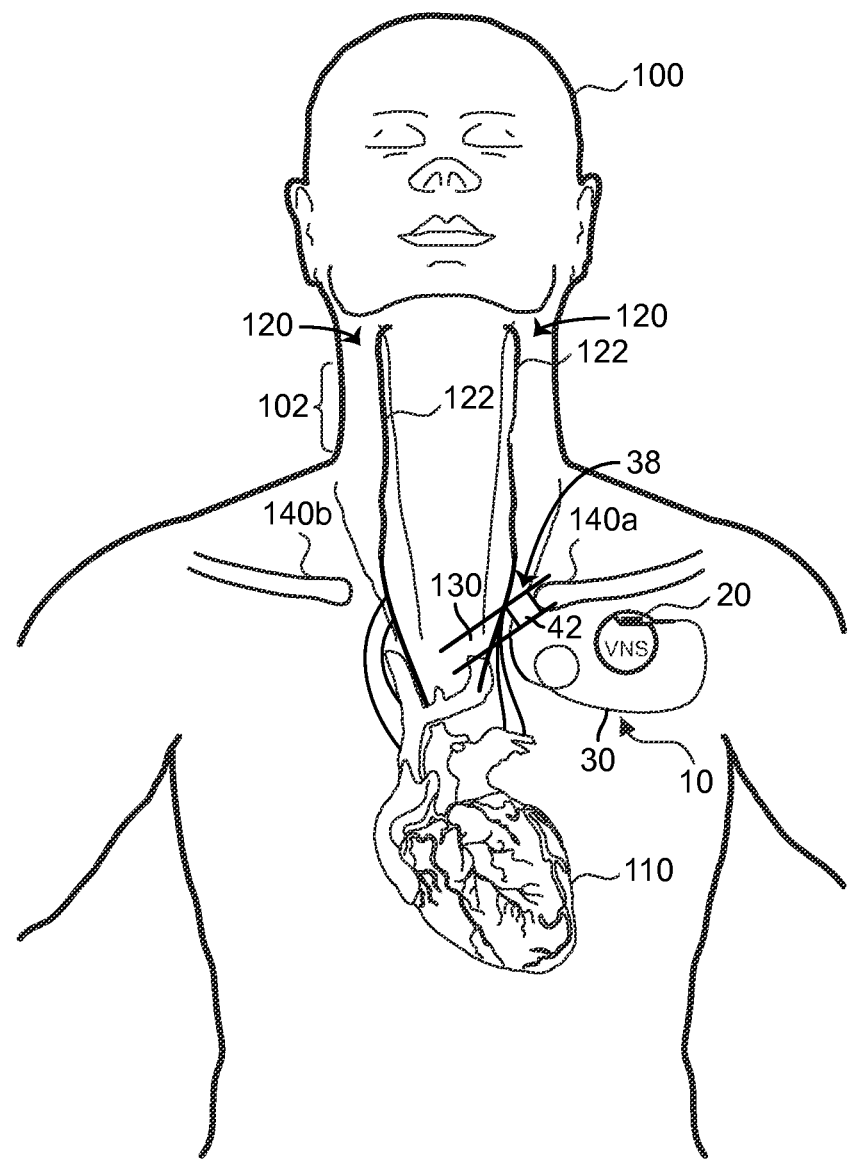
FIG. 3B is an illustration of the nerve stimulation device of FIG. 1 implanted within a patient to provide vagus nerve stimulation to the vagus nerve endovascularly through the venous system, according to an exemplary embodiment.
Figure 3C:
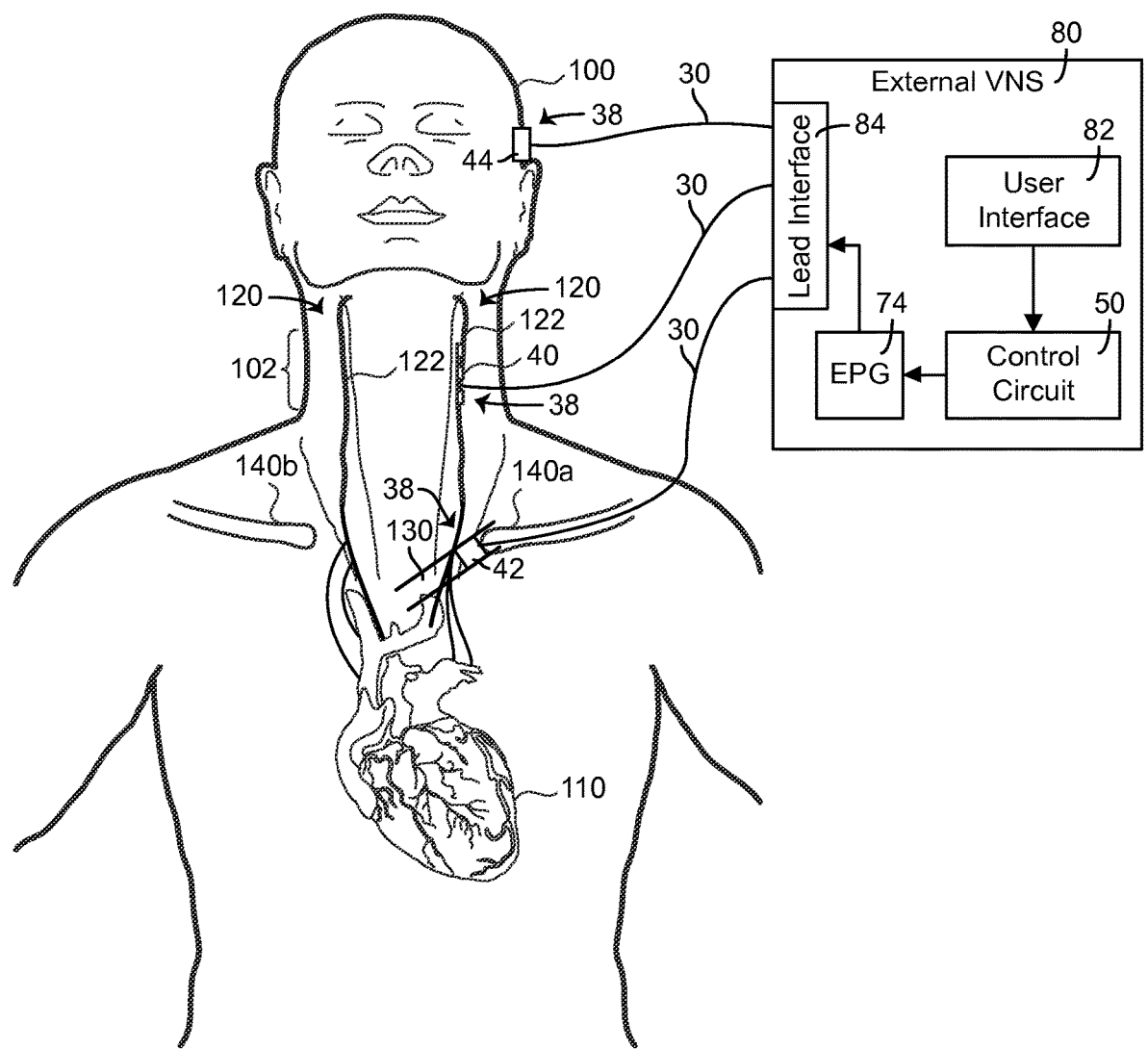
FIG. 3C is an illustration of the nerve stimulation device of FIG. 1 positioned outside the body of a patient to provide vagus nerve stimulation, according to an exemplary embodiment.

As shown in FIGS. 1 and 3A-3B, the vagus nerve stimulator 10 may include a neurostimulator, shown as implantable neurostimulator 20, and a therapy lead, shown as lead 30. As shown in FIG. 3C, the vagus nerve stimulator 10 may include a neurostimulator, shown as external neurostimulator 80. According to an exemplary embodiment, the implantable neurostimulator 20 and/or the external neurostimulator 80 are configured to generate an electrical signal that the lead 30 delivers to a desired location (e.g., the vagus nerve, etc.). As shown in FIG. 1, the implantable neurostimulator 20 includes a housing, shown as hermetically sealed housing 22. According to an exemplary embodiment, the hermetically sealed housing 22 is manufactured from a biocompatible, implantation-safe material (e.g., titanium, etc.). The implantable neurostimulator 20 includes a connector cover, shown as header 24, coupled to the hermetically sealed housing 22. The header 24 is portioned to enclose a connection interface, shown as receptacle 26.

The lead 30 includes a wire, shown as lead wire 32. In one embodiment, the lead wire 32 includes a silicone-insulated alloy conductor material. The lead 30 includes a connector, shown as a lead connector 34, positioned on a proximal end of the lead wire 32. As shown in FIG. 1, the lead connector 34 transitions from an insulated electrical lead body to a connection interface, shown as connector pin 36 (e.g., a metal connector pin, etc.). In one embodiment, the lead connector 34 is manufactured using silicone and the connector pin 36 is made of stainless steel, although other suitable materials may be used as well. According to an exemplary embodiment, the connector pin 36 is configured to be received by the receptacle 26 of the implantable neurostimulator 20 to couple the lead 30 thereto. During implantation, the connector pin 36 is guided through the receptacle 26 into the header 24 and securely fastened in place using a fastener, shown as set screws 28, thereby electrically coupling the lead 30 to the implantable neurostimulator 20. In one embodiment, the header 24 encloses the receptacle 26 into which a single connector pin 36 for the lead 30 may be received. In other embodiments, two or more receptacles 26 may also be provided, to couple additional leads 30 to the implantable neurostimulator 20.

As shown in FIGS. 1-3C, the lead 30 includes a simulation element, shown as electrode 38. As shown in FIGS. 1 and 3A-3C, the electrode 38 is positioned on a distal end of the lead wire 32. According to the exemplary embodiment shown in FIGS. 1 and 3A, the electrode 38 includes a cuff-type electrode 40. In other embodiments, the electrode 38 includes another type of electrode (e.g., a pig-tail or helical electrode, etc.). In some embodiments, another type of lead is used (e.g., a stent, a pig-tail lead, a preformed lead, etc.). According to the exemplary embodiment shown in FIG. 3B, the electrode 38 includes an endovascular electrode 42. According to the exemplary embodiment shown in FIG. 3C, the electrode 38 may include the cuff-type electrode 40, the endovascular electrode 42, and/or an external electrode 44. According to an exemplary embodiment, the electrode 38 is configured to deliver an electrical signal from the implantable neurostimulator 20 and/or the external neurostimulator 80 to a desired location (e.g., the vagus nerve, etc.).

Figure 2:
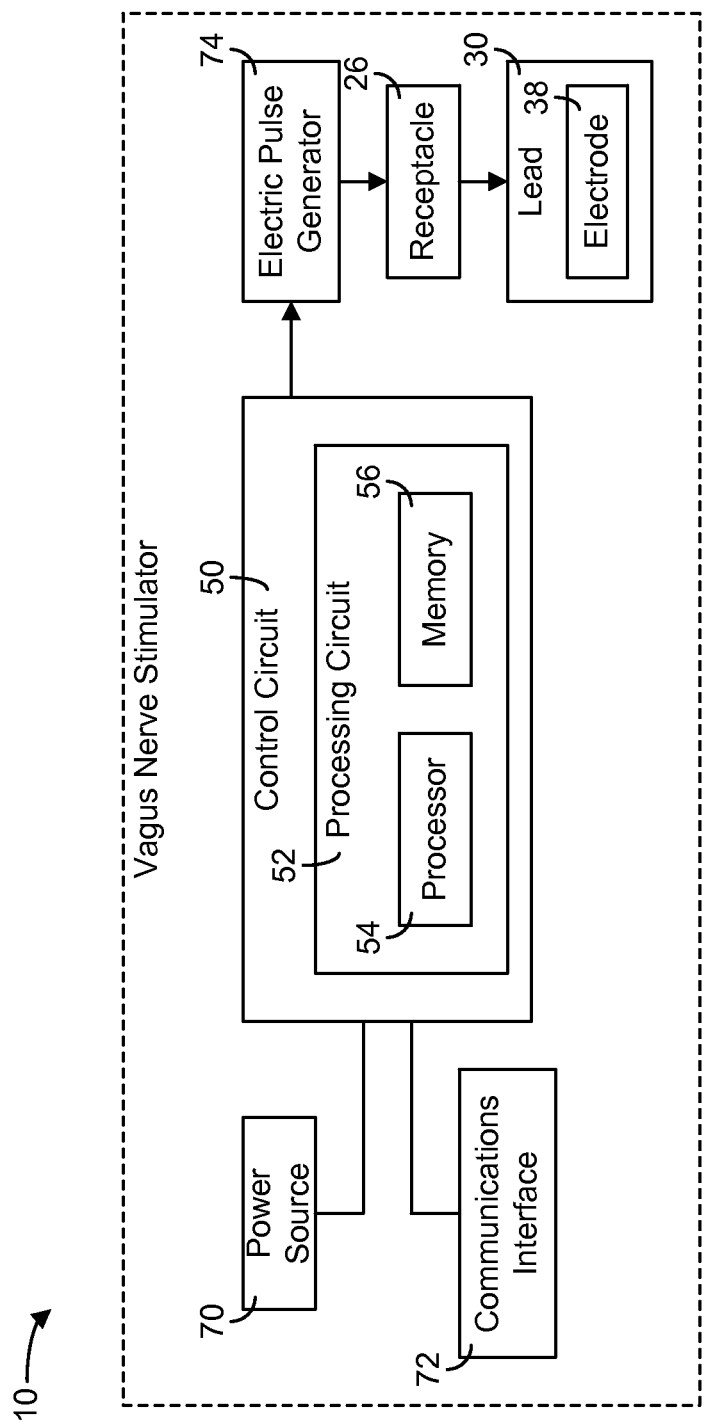
FIG. 2 is schematic block diagram of the nerve stimulation device of FIG. 1, according to an exemplary embodiment.

As shown in FIGS. 1-2, the implantable neurostimulator 20 includes (e.g., contained within the hermetically sealed housing 22, etc.) electronic circuitry, shown as control circuit 50, an energy storage device, shown as power source 70, a communications interface, shown as communications interface 72, and a pulse generator, shown as electric pulse generator 74. The power source 70 is configured to power the implantable neurostimulator 20 (e.g., the control circuit 50, the electric pulse generator 74, the communications interface 72, etc.). In some embodiments, the power source 70 includes a lithium carbon monoflouride battery. In other embodiments, the power source 70 includes another type of battery (e.g., a lithium-ion battery, a nickel-metal hydride battery, etc.). According to an exemplary embodiment, the communications interface 72 is configured to provide remote access to the operation of the implantable neurostimulator 20 using an external programmer, a simple patient magnet, and/or an electromagnetic controller. In one embodiment, the communications interface 72 includes a Reed circuit. In some embodiments, the communications interface 72 includes a transceiver that remotely communicates with the external programmer using a wireless communication protocol (e.g., radio frequency signals, Bluetooth, etc.) to receive programming instructions and/or transmit telemetry information to the external programmer or other external device. In some embodiments, other components, such as an integrated heart rate sensor and/or an accelerometer, may be integrated within the implantable neurostimulator 20.

According to an exemplary embodiment, the control circuit 50 is configured to control the electric pulse generator 74 to generate electric pulses to be delivered by the lead 30 (e.g., the electrode 38, etc.) to provide stimulation to a desired location (e.g., the vagus nerve, etc.). Thereby, the implantable neurostimulator 20 may deliver eVNS and/or VNS under control of the control circuit 50 based on stored stimulation parameters that are programmable (e.g., by a physician, by the manufacturer, etc.). Each stimulation parameter may be independently programmed to define the characteristics of the cycles of therapeutic stimulation and inhibition to ensure optimal stimulation for a patient. The programmable stimulation parameters may include output current, signal frequency, pulse width, signal ON time, signal OFF time, magnet activation (e.g., for eVNS and/or VNS specifically triggered by "magnet mode", etc.), and/or reset parameters. The stimulation parameters may be synchronous, asynchronous, and/or pulsed. Other programmable parameters are possible. In addition, sets or "profiles" of reselected stimulation parameters may be provided to physicians with the external programmer and fine-tuned to a patient's physiological requirements prior to being programmed into the implantable neurostimulator 20.

The implantable neurostimulator 20 may be interrogated prior to implantation and throughout the therapeutic period with a healthcare provider-operable external programmer and programming wand for checking proper operation, downloading recorded data, diagnosing problems, and programming operational parameters. In some embodiments, use of the external programmer is restricted to healthcare providers, while more limited manual control is provided to the patient through "magnet mode." In one embodiment, the external programmer executes application software specially designed to interrogate the implantable neurostimulator 20. The programming computer may interface to the programming wand through a standardized or proprietary wired or wireless data connection. Other configurations and combinations of external programmer, programming wand, and/or application software are possible.

As shown in FIG. 2, the control circuit 50 of the vagus nerve stimulator 10 includes a processing circuit 52. The processing circuit 52 includes a processor 54 and a memory 56. The processor 54 may be implemented as a general-purpose processor, a micro-processor, an application specific integrated circuit (ASIC), one or more field programmable gate arrays (FPGAs), a digital signal processor (DSP), a group of processing components, or other suitable electronic processing components. The memory 56 (e.g., RAM, ROM, Flash Memory, hard disk storage, etc.) may store data and/or computer code for facilitating the various processes described herein. Thus, the memory 56 may be communicably connected to the processor 54 and provide computer code or instructions to the processor 54 for executing the processes described in regard to the vagus nerve stimulator 10 herein. Moreover, the memory 56 may be or include tangible, non-transient volatile memory or non-volatile memory. In some embodiments, the memory 56 may include database components, object code components, script components, or any other type of information structure for supporting the various activities and information structures described herein.

The memory 56 may include various modules for completing processes described herein. More particularly, the memory 56 includes modules configured to control operation of the vagus nerve stimulator 10 to provide ART via VNS and/or eVNS. The memory 56 may store a control program that operates the vagus nerve stimulator 10 according to stored stimulation parameters and timing cycles (e.g., a predefined stimulation protocol, etc.). For example, the memory 56 may include a voltage module that regulates system power, a stimulation module that controls the overall pulse generator function, an input module that receives and implements programming commands from the external programmer or other external source, and/or data module that collects and stores telemetry information, among other possible modules that perform additional or alternative functions. While various modules with particular functionality may be used, it will be understood that the memory 56 may include any number of modules for completing the functions described herein. For example, the activities of multiple modules may be combined as a single module and additional modules with additional functionality may be included. Further, it will be understood that the processing circuit 52 of the vagus nerve stimulator 10 may further control other processes beyond the scope of the present disclosure.

According to the exemplary embodiments shown in FIGS. 3A-3B, the implantable neurostimulator 20 is implanted into the right or left pectoral region of a patient 100. Generally, the implantable neurostimulator 20 is implanted on the same side (ipsilateral) of the patient's body as the vagus nerve 120 to be stimulated (e.g., right or left vagus nerve 120, etc.). Although other neurostimulator-vagus nerve configurations, including contra-lateral and bi-lateral, are possible. As shown in FIG. 3A, the cuff-type electrode 40 is implanted on the main trunk 122 of the vagus nerve 120 about halfway between the clavicle 140*a-b* and the mastoid process (e.g., at the cervical level, etc.). The lead 30 and cuff-type electrodes 40 may be implanted by first exposing the carotid sheath and chosen vagus nerve 120 through a latero-cervical incision on the ipsilateral side of the neck 102 of the patient 100. The cuff-type electrodes 40 are then placed onto the exposed nerve sheath and tethered. A subcutaneous tunnel is formed between the respective implantation site of the implantable neurostimulator 20 and cuff-type electrode 40, through which the lead 30 is guided to the implantable neurostimulator 20 and securely connected. Such an implantation requires an invasive surgical procedure under general anesthesia to position the implantable neurostimulator 20 to deliver stimulation directly to the vagus nerve 120 and provide VNS therapy to the patient.

Once implantation of the vagus nerve stimulator 10 is completed, the implantable neurostimulator 20 may provide VNS directly to the main truck 122 of the vagus nerve 120 with the cuff-type electrode 40. The stimulation produces action potentials in the underlying nerves that propagate bi-directionally. Both sympathetic and parasympathetic nerve fibers are stimulated through the cuff-type electrode 40 of the vagus nerve stimulator 10. Stimulation of the cervical vagus nerve 120 results in propagation of action potentials in both afferent and efferent directions from the site of stimulation to restore autonomic balance. Afferent action potentials propagate toward the parasympathetic nervous system's origin in the medulla in the nucleus ambiguus, nucleus tractus solitarius, and the dorsal motor nucleus, as well as towards the sympathetic nervous system's origin in the intermediolateral cell column of the spinal cord. Efferent action potentials propagate toward the heart 110 to activate the components of the heart's intrinsic nervous system. Either the left or right vagus nerve 120 may be stimulated by the vagus nerve stimulator 10, although stimulation of the right vagus nerve 120 has a moderately stronger effect on heart rate (e.g., on the order of approximately 20% stronger) than left vagus nerve 120 stimulation at the same parametric levels.

At the cervical level, the vagus nerve 120 contains afferent fibers but also efferent ones innervating most of the intra-thoracic and abdominal organs as well as the laryngeal area through the recurrent laryngeal nerve which is included with the vagus nerve 120 in the neck 102. Stimulating the vagus nerve 120 in the cervical region may lead to adverse effects, related to large innervated areas, including cough, voice alteration and hoarseness, pain, dyspnea, nausea, etc. In heart failure, the expected effect of the stimulation may be mainly efferent (i.e. directed to the heart 110). Therefore, the closer the stimulation site may be to the heart 110, the greater the desired effects may be, while avoiding adverse effects. However, a direct approach of the vagus nerve 120 at the thoracic level also requires an invasive surgery, similar to at the cervical level.

Figure 4A:
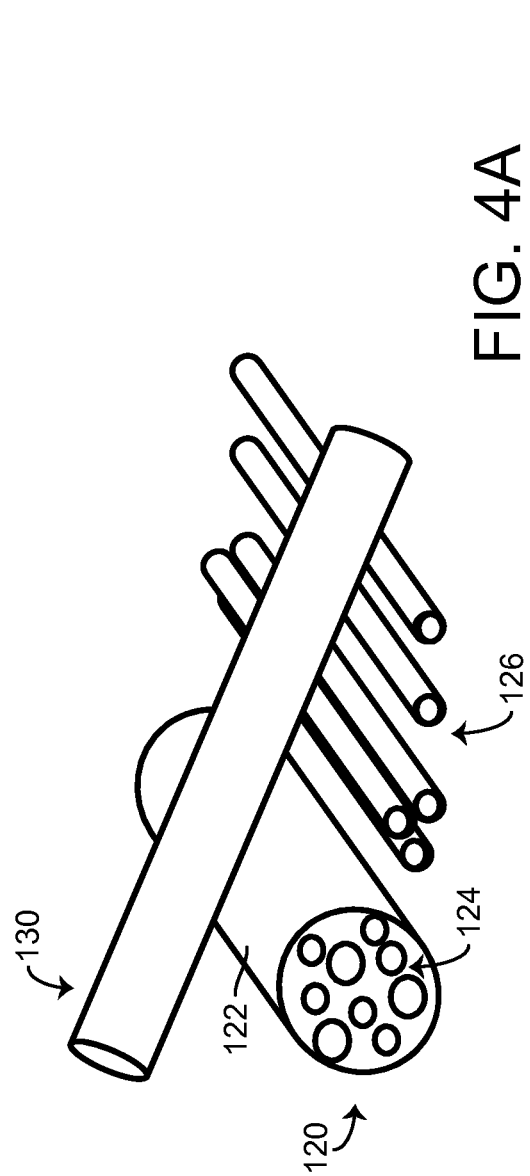
FIG. 4A is an illustration of the vagus nerve, according to an exemplary embodiment.
Figure 4B:
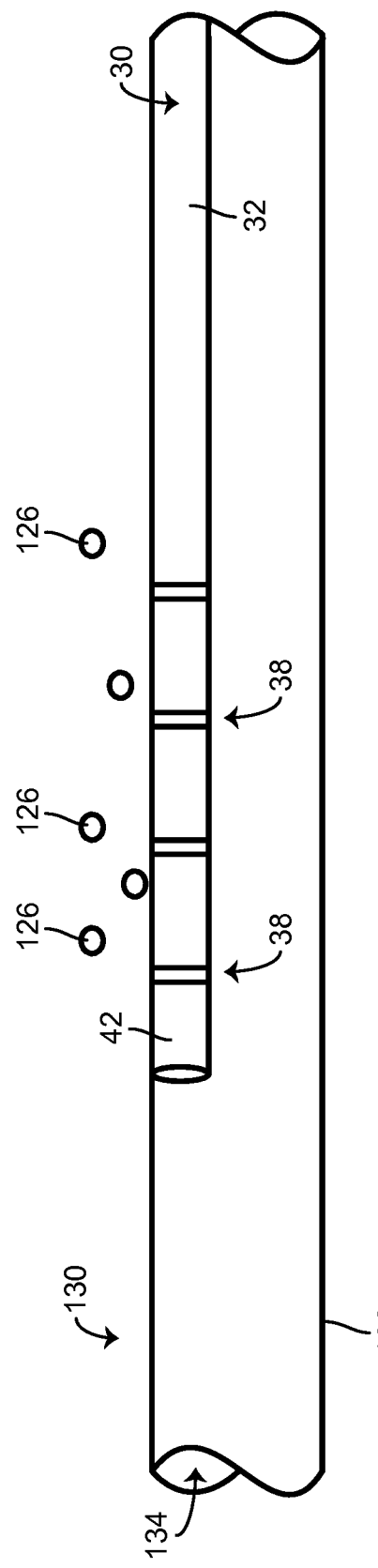
FIG. 4B is an illustration of the lead of FIG. 1 positioned within a vein of a patient to provide endovascular vagus nerve stimulation, according to an exemplary embodiment.

Referring now to FIGS. 3B and 4A-4B, at the cervical level, each vagus nerve 120 (right and left) is mainly organized around a single main trunk 122 having main fascicles 124 disposed therein. The main trunk 122, however, splits into several branches innervating the organs. At the thoracic level, some branches or fascicles, shown as cardiac fascicles 126, leave the main trunk 122 to target the cardiac tissues. Stimulation of the cardiac fascicles 126 cannot be realized by a traditional cuff-type electrode. However, the vagus nerve 120 goes along various vascular structures (e.g., including the azygos vein, etc.) in the thoracic level. Therefore, stimulation may be attempted through the walls of the vessels. Anatomically, the cardiac fascicles 126 are in close relationship with various vascular structures of the venous system, including the cross of the azygos vein, the superior vena cava, and the pulmonary artery.

By way of example, the lead 30 (e.g., a longitudinal lead, a stent, a preformed lead, a pig tail lead, etc.) may be endovascularly positioned within the venous system to provide eVNS. In practice, the cardiac fascicles 126 consist of several fascicles, not identical in all humans. Therefore, such an endovascular lead 30 may have one or more electrodes positioned along the lead wire 32 to provide VNS transvascularly through the venous system (e.g., through the walls of the superior vena cava, the pulmonary artery, the azygos vein, etc.) to cardiac fascicles 126 of the vagus nerve 120 (i.e., endovascular vagus nerve stimulation (eVNS)). The endovascular or transvenous stimulation may be used to stimulate some nerves, including the vagus nerve 120 (e.g., the main trunk 122, the cardiac fascicles 126, etc.). EVNS may provide various advantages over VNS (e.g., compared to direct access to the vagus nerve 120 with a cuff-type electrode, etc.) including, but not limited to, the absence of invasive surgery and the absence of the undesired stimulation of the recurrent laryngeal nerve. The placement of the endovascular lead(s) 30 may be realized by the catheterization of a vein (e.g., through an easily accessible vein, similar as in a pacemaker procedure, under fluoroscopy, etc.).

As shown in FIGS. 3B and 4B, the lead wire 32 of the lead 30 is endovascularly positioned within an interior, shown as vein lumen 134, of a vascular structure, shown as vein 130 (e.g., the azygos vein, etc.). By way of example, the azygos vein may be easily accessible from the vena cava of the heart 110 which allows for the electrical stimulation of the cardiac fascicles 126. The lead 30 may include the endovascular electrode 42 having one or more electrodes 38 positioned along the length of the lead wire 32 (e.g., at an end thereof, etc.) and may be in contact with a wall, shown as vein wall 132, of the vein 130. According to an exemplary embodiment, a plurality of electrodes 38 facilitate increasing the stimulation of the small and non-uniformly scattered cardiac fascicles 126 with the lead 30 (e.g., since the location and number of cardiac fascicles 126 varies from patient to patient, etc.). Thus, the lead 30 of FIG. 4B positioned within the vein lumen 134 may facilitate the stimulation of the cardiac fascicles 126 transvascularly through the vein wall 132 of the vein 130, thereby providing eVNS to a vagus nerve 120 of the patient.

Referring now to FIG. 3C, the external neurostimulator 80 is configured to be positioned externally from the body of the patient 100. In one embodiment, the external neurostimulator 80 is a stationary device configured to perform various evaluation procedures (e.g., for testing the suitability of patients to receive the implantable neurostimulator 20, etc.). In other embodiments, the external neurostimulator 80 is configured as a portable device that is wearable or capable of being carried with the patient 100. As shown in FIG. 3C, the external neurostimulator 80 includes a user interface 82, the control circuit 50, the electric pulse generator 74, and a lead interface 84. The user interface 82 may enable a user of the external neurostimulator 80 to communicate with the vagus nerve stimulator 10 and other components thereof (e.g., the electric pulse generator 74, the control circuit 50, etc.). The user interface 82 may include an input device and/or a display device. The input device may be configured to allow a user to control the vagus nerve stimulator 10. The input device may include, but is not limited to, a keyboard, a mouse, a touchscreen device, one or more buttons and switches, voice command receivers, a connected portable device (e.g., a smart phone, a tablet, a laptop, etc.), etc. The display device may be configured to provide a graphical user interface (GUI) to the user of the vagus nerve stimulator. The display device may include, but is not limited to, a touch-screen display, a projector and projection screen, a monitor or television (e.g., a LCD, LED, plasma, DLP, etc.), augmented reality glasses, a portable device (e.g., a smartphone, tablet, laptop, etc.), and/or any other known display devices that can provide a GUI. The lead interface 84 may be configured to facilitate coupling one or more leads 30 to the external neurostimulator 80 (e.g., similar to the receptacle 26 of the implantable neurostimulator 20, etc.).

Although not shown in FIG. 3C, it can be appreciated that an external neurostimulator 80 may include all or a portion of the components used with the implantable neurostimulator 20 (e.g., the power source 70, the communications interface 72, etc.). Since the external neurostimulator 80 may be configured for placement and use outside of the body of the patient 100, the components of the external neurostimulator 80 may not require the hermetically sealed housing 22 and may be incorporated into another external medical device such as an external patient monitoring or an external therapy-delivering device, or may be configured to have a disengageable coupling between the external neurostimulator 80 and components that contact the human body.

As shown in FIG. 3C, the external neurostimulator 80 may be coupled to one or more leads 30. The one or more leads 30 may include various electrodes 38 positioned to provide vagus nerve stimulation to the vagus nerve 120. In some embodiments, the lead 30 includes the cuff-type electrode 40 positioned on the vagus nerve 120 such that the external neurostimulator 80 may provide VNS therapy directly to the main truck 122 of the vagus nerve 120. In some embodiments, the lead 30 includes the endovascular electrode 42 positioned within the vein 130 such that the external neurostimulator 80 may provide VNS therapy transvascularly to the vagus nerve 120 through the vein 130 (e.g., the azygos vein, etc.). In some embodiments, the lead 30 includes the external electrode 44 positioned outside of the body of the patient 100 on a peripheral nerve of the patient 100 that communicates with the vagus nerve 120, with the stimulation energy delivered through the skin of the patient 100 near, for example, the ear (e.g., auricular VNS stimulation, etc.).

In one embodiment, the implantable neurostimulator 20 and/or the external neurostimulator 80 include one or more cardiac leads having sensors configured to facilitate monitoring activity of the heart 110 (e.g., heart rate, blood pressure, heart rate variability, ejection fraction, resting heart rate, nocturnal heart rate, diastolic filling time, etc.). Such cardiac leads may be used in any of the aforementioned embodiments shown in and described in relation to FIGS. 3A-3C. The one or more cardiac leads may be positioned on, within, and/or near the heart 110 (e.g., an implanted cardiac lead) and/or external to the body of the patient 100 (e.g., on a chest of the patient proximate the heart 110). In some embodiments, the implantable neurostimulator 20 additionally or alternatively includes an accelerometer and/or other sensors (e.g., positioned within the hermetically sealed housing 22) configured to collect cardiac activity data and/or patient activity data (e.g., regarding activity including moving, walking, running, sleeping, resting, etc. of the patient 100). The control circuit 50 of the vagus nerve stimulator 10 may receive and process information (e.g., cardiac activity data, physical activity data, etc.) from the one or more cardiac leads and/or other devices (e.g., accelerometers). In some embodiments, the control circuit 50 is configured to synchronize the vagus nerve stimulation provided by the electrode 38 of the lead 30 with cardiac pulses of the heart 110 and/or otherwise control the vagus nerve stimulation based on the cardiac activity data (e.g., received from the one or more cardiac leads, accelerometers, etc.) and/or the patient activity data (e.g., received from accelerometers and/or other devices). In some embodiments, the control circuit 50 is configured to store the cardiac activity data and/or the physical activity data for future use (e.g., to be downloaded by a physician, to track cardiac activity over time, to build a histogram, etc.).

In another embodiment, the vagus nerve stimulator 10 includes one of (i) the implantable neurostimulator 20 and (ii) the external neurostimulator 80 and may be used in combination with a cardiac monitoring device configured to monitor activity of the heart 110. The cardiac monitoring device may be an implantable device (e.g., similar to the implantable neurostimulator 20) or an external device (e.g., similar to the external neurostimulator 80). The cardiac monitoring device may include one or more cardiac leads, an external sensor, an accelerometer, and/or still another device configured to monitor the cardiac activity of the heart 110 (e.g., acquire cardiac activity data) and/or the physical activity of the patient (e.g., acquire physical activity data). The cardiac monitoring device may include an independent control circuit (e.g., similar to the control circuit 50 of the vagus nerve stimulator 10) configured to store the cardiac activity data and/or the physical activity data for future use (e.g., to be downloaded by a physician, to track cardiac activity over time, to build a histogram, etc.). In some embodiments, the cardiac monitoring device is configured to communicate with the vagus nerve stimulator 10 (e.g., via a wired communication protocol, a wireless communication protocol, etc.) such that the vagus nerve stimulator 10 may control the vagus nerve stimulation based at least in part on the cardiac activity data (e.g., synchronize the vagus nerve stimulation provided by the electrode 38 of the lead 30 with cardiac pulses of the heart 110 monitored by the cardiac monitoring device) and/or the physical activity data.

However, as described above, autonomic regulation therapy (ART) via vagus nerve stimulation may not be suitable for some patients. Thus, prior to the implantation of the implantable neurostimulator 20 of vagus nerve stimulator 10 or prior to the implantation of a lead 30 of the external neurostimulator 80, patients can be evaluated for various characteristics and/or response parameters to determine whether a patient is a good candidate to receive ART through VNS and/or eVNS (e.g., based on inclusion and/or exclusion criteria, etc.). Proper patient selection may increase the success of ART and the efficacy of the VNS and/or eVNS treatment.

By way of example, determining which patients may respond well to VNS and/or eVNS, and which may not, may be based on one or more physiological characteristics of the patient (e.g., compared to inclusion/exclusion criteria, etc.) determined using non-invasive techniques. By way of another example, determining which patients may respond well to VNS and/or eVNS, and which may not, may be based on a physiological response of the patient (e.g., compared to inclusion/exclusion criteria, etc.) during a stimulation test (e.g., using eVNS, external VNS methods including auricular VNS, direct VNS, etc.). In some embodiments, determining which patients may respond well to VNS and/or eVNS is based on a combination of the one or more physiological characteristics and the physiological response of the patient during a stimulation test.

Figure 5:
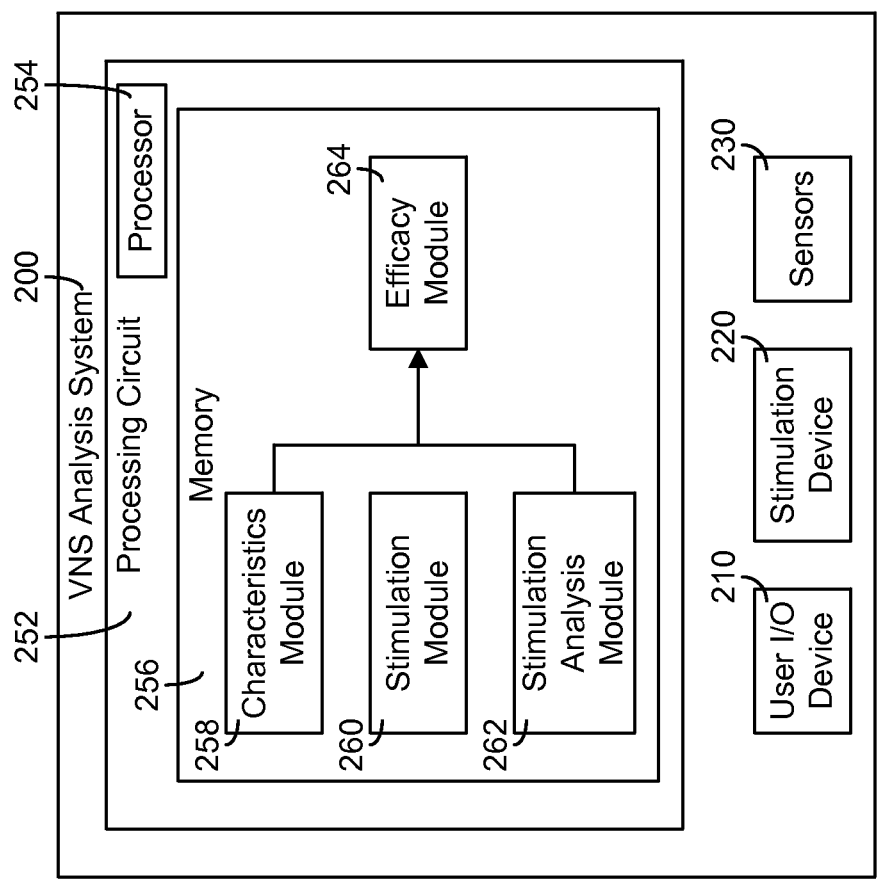
FIG. 5 is schematic block diagram of a vagus nerve stimulation analysis system, according to an exemplary embodiment.

As such, referring now to FIG. 5, a VNS analysis system 200 may be used to facilitate assessing a patient's suitability for receiving vagus nerve stimulation therapy (e.g., determining which patients may positively respond to eVNS and/or VNS, and which may negatively respond to eVNS and/or VNS; predicting the potential efficacy of eVNS and/or VNS provided by the vagus nerve stimulator 10 prior to surgical implantation; etc.). As shown in FIG. 5, the VNS analysis system 200 includes a user input/output (I/O) device 210, a stimulation device 220, one or more sensors 230, and a processing circuit 252.

The user I/O device 210 may enable a user of the VNS analysis system 200 to communicate with the VNS analysis system 200 and other components thereof (e.g., the stimulation device 220, etc.). In some embodiments, the user I/O device 210 is communicably coupled to the VNS analysis system 200 via a wireless communication protocol (e.g., Bluetooth, Zigbee, Wi-Fi, radio, cellular, etc.). In some embodiments, the user I/O device 210 is directly communicably coupled to the VNS analysis system 200 (e.g., with a wired connection, etc.). The user I/O device 210 may include an input device and/or a display device. The input device may be configured to allow a user to control the VNS analysis system 200 and/or input various parameters (e.g., characteristics of the patient, criteria, etc.). The input device may include, but is not limited to, a keyboard, a mouse, a touchscreen device, one or more buttons and switches, voice command receivers, a portable device (e.g., a smart phone, a tablet, a laptop, etc.), etc. The display device may be configured to provide a graphical user interface (GUI) to the user of the VNS analysis system 200. The display device may include, but is not limited to, a touchscreen display, a projector and projection screen, a monitor or television (e.g., a LCD, LED, plasma, DLP, etc.), augmented reality glasses, a portable device (e.g., a smartphone, tablet, laptop, etc.), and/or any other known display devices that can provide a GUI.

The stimulation device 220 may be configured to provide stimulation (e.g., acute, temporary, etc.) during a pre-screening evaluation for assessing a patient's response to vagus nerve stimulation therapy. In one embodiment, the stimulation device 220 includes a lead (e.g., the lead 30, etc.) having at least one electrode (e.g., the electrodes 38, etc.) configured to be endovascularly positioned within the vein lumen 134 of the vein 130 (e.g., the azygos vein, etc.) proximate a portion of the vagus nerve 120 (e.g., the cardiac fascicles 126 that branch from the vagus nerve 120, etc.). Thereby, the stimulation device 220 may provide the stimulation transvacularly through the vein wall 132 of the vein 130 to the vagus nerve 120 (e.g., indirectly, eVNS, etc.). In another embodiment, the stimulation device 220 includes an external stimulation device configured to be positioned outside the body of the patient to provide the stimulation through the skin of the patient. In one embodiment, the external stimulation device includes an auricular stimulation device configured to provide auricular stimulation around and/or near an ear of the patient. In other embodiments, the external stimulation device includes another type of stimulation device configured to provide stimulation to another external area of the patient (e.g., the chest, the back, the neck, etc.). In still other embodiments, the stimulation device 220 includes a cuff-type electrode (e.g., the cuff-type electrode 40, etc.) or another type of electrode temporarily implanted onto the vagus nerve 120 and configured to provide stimulation directly to the vagus nerve 120 (e.g., VNS, etc.). By way of example, such an invasive VNS testing method may be used while a patient is already undergoing a surgical procedure that allows for such invasive testing to occur without requiring an additional or minimal surgical manipulation to access the vagus nerve (e.g., the reason for performing the surgical procedure is not performed to facilitate the VNS testing, the VNS testing is an additional step included in another procedure, etc.).

The sensors 230 may be configured to acquire response data of a patient undergoing pre-implantation testing and assessment to facilitate monitoring a physiological response of the patient to vagus nerve stimulation therapy. The response data may include data indicative of a physiological response of the patient to stimulation provided by the stimulation device 220 to the vagus nerve 120. The sensors 230 may facilitate monitoring one or more physiological responses of the patient including heart rate change, heart rate variability, breathing patterns, induced pain, and/or blood pressure changes, among other possible responses induced by the stimulation. The sensors 230 may also be configured to monitor stimulation levels of the electrode(s) 38 (e.g., current, voltage, power, signal frequency, pulse width, signal ON time, signal OFF time, synchronous stimulation, asynchronous stimulation, pulsed stimulation, etc.). The sensors 230 may additionally or alternatively be configured to acquire patient data indicative of one or more physiological characteristics of the patient prior to stimulation. The one or more physiological characteristics acquired by the sensors 230 may include resting heart rate, nocturnal heart rate, heart rate variability (HRV), inflammation levels, left ventricular ejection fraction (EF), brain natriuretic peptide (BNP) levels, heart failure etiology (i.e., ischemic vs. non-ischemic), and/or existence of autonomic dysfunction, among other possible measureable physiological characteristics.

As shown in FIG. 5, the processing circuit 252 includes a processor 254 and a memory 256. The processor 254 may be implemented as a general-purpose processor, an application specific integrated circuit (ASIC), one or more field programmable gate arrays (FPGAs), a digital signal processor (DSP), a group of processing components, or other suitable electronic processing components. The memory 256 (e.g., RAM, ROM, Flash Memory, hard disk storage, etc.) may store data and/or computer code for facilitating the various processes described herein. Thus, the memory 256 may be communicably connected to the processor 254 and provide computer code or instructions to the processor 254 for executing the processes described in regard to the VNS analysis system 200 herein. Moreover, the memory 256 may be or include tangible, non-transient volatile memory or non-volatile memory. In some embodiments, the memory 256 may include database components, object code components, script components, or any other type of information structure for supporting the various activities and information structures described herein.

The memory 256 may include various modules for completing processes described herein. More particularly, the memory 256 includes modules configured to control operation of the VNS analysis system 200 to assess a patient's suitability for receiving vagus nerve stimulation therapy prior to the implantation of the vagus nerve stimulator 10. While various modules with particular functionality may be used, it will be understood that the memory 256 may include any number of modules for completing the functions described herein. For example, the activities of multiple modules may be combined as a single module and additional modules with additional functionality may be included. In some embodiments, the modules of the memory 256 are integrated and/or combined. Further, it will be understood that the processing circuit 252 of the VNS analysis device may further control other processes beyond the scope of the present disclosure.

As shown in FIG. 5, the VNS analysis system 200 includes a characteristics module 258, a stimulation module 260, a stimulation analysis module 262, and an efficacy module 264. The characteristics module 258 may be configured to receive and store patient data indicative of various physiological characteristics of a patient being assessed for the suitability of vagus nerve stimulation therapy. The physiological characteristics may include an indication of age, HRV, inflammation, left ventricular EF, BNP levels, heart failure etiology, resting heart rate, nocturnal heart rate, age, the existence of autonomic dysfunction, and/or the existence of cardiac resynchronization therapy (CRT), among other possible physiological characteristics of the patient (e.g., blood pressure, weight, height, gender, etc.). In some embodiments, at least a portion of the physiological characteristics are manually input and received by the characteristics module 258 from an operator of the VNS analysis system 200 via the user I/O device 210 (e.g., age, existence of CRT, existence of autonomic dysfunction, resting heart rate, etc.). In some embodiments, at least a portion of the physiological characteristics are received by the characteristics module 258 from the sensors 230 (e.g., resting heart rate, nocturnal heart rate, left ventricular EF, HRV, existence of autonomic dysfunction, etc.). In some embodiments, at least a portion of the physiological characteristics are received by the characteristics module 258 from a remote server or device (e.g., downloaded therefrom, etc.). As shown in FIG. 5, the characteristics module 258 is communicably coupled to the efficacy module 264. Thus, the characteristics module 258 may provide the physiological characteristics to the efficacy module 264 to perform further analysis.

The efficacy module 264 may be configured to receive and store one or more criteria (e.g., screening parameters, etc.) regarding a patient's suitability for receiving vagus nerve stimulation therapy. The one or more criteria may be predefined within the efficacy module 264 and/or manually input by an operator of the VNS analysis system 200. The one or more criteria may include an age range or threshold, a resting heart rate threshold, a nocturnal heart rate threshold, ischemic heart failure versus non-ischemic heart failure, existing cardiac resynchronization therapy, a BNP threshold, a left ventricular EF threshold or range, a HRV threshold, autonomic dysfunction, and/or an inflammation threshold. The efficacy module 264 may thereby be configured to receive the physiological characteristics of a respective patient from the characteristics module 258 to determine the patient's suitability for receiving vagus nerve stimulation therapy based on the one or more criteria and the one or more physiological characteristic of the patient being assessed for vagus nerve stimulation therapy. In some embodiments, the one or more criteria may be set or selected based on various characteristics of the patient including age, gender, height, weight, blood pressure, and/or cholesterol levels (e.g., the criteria may be dynamic, not static).

In some embodiments, the efficacy module 264 is configured to compare an age of the patient to an age threshold and/or an age range. By way of example, age may impact the signal conduction on nerves and/or brain plasticity, which may reduce the efficacy of vagus nerve stimulation therapy. According to an exemplary embodiment, the efficacy module 264 is configured to determine a patient is more suitable for vagus nerve stimulation therapy in response to the age of the patient being less than a maximum age threshold. In one embodiment, the maximum age threshold is 90 years old. In other embodiments, the maximum age threshold is 80 years old. In still other embodiments, the maximum age threshold is less than 80 years old (e.g., 75, 65, etc.). According to another exemplary embodiment, the efficacy module 264 is configured to determine a patient is more suitable for vagus nerve stimulation therapy in response to the age of the patient being greater than a minimum age threshold. In one embodiment, the minimum age threshold is 18 years old. In other embodiments, the minimum age threshold is 30 years old. In still other embodiments, the minimum age threshold is greater than 30 years old (e.g., 35, 45, etc.). According to still another exemplary embodiment, the efficacy module 264 is configured to determine a patient is more suitable for vagus nerve stimulation therapy in response to the age of the patient being within the age range (e.g., the minimum age of the age range may be 18, 25, 30, 40, etc.; the maximum age of the age range may be 65, 70, 75, 80, 85, 90, etc.). The efficacy module 264 may be further configured to assign a first value or first classification to patients that satisfy the minimum age threshold, the maximum age threshold, and/or the age range, and assign a second value or second classification to patients that do not satisfy the minimum age threshold, the maximum age threshold, and/or the age range. The first value or first classification may include a greater weight than the second value or second classification (e.g., for use with the combination of other characteristics when determining a composite weighted score). Alternatively, the efficacy module 264 may assign a value from a range of values based on the patient's age relative the minimum age threshold, the maximum age threshold, and/or the age range (e.g., a higher value the further away from the maximum age threshold, a lower value the closer to the maximum age threshold, etc.).

In some embodiments, the efficacy module 264 is configured to compare a resting heart rate of the patient to a resting heart rate threshold. By way of example, patients with a high resting heart rate (e.g., despite OMT) may be under high sympathetic drive and may be more sensitive to (e.g., more suitable for receiving) vagus nerve stimulation therapy based on the accentuated antagonism mechanism. According to an exemplary embodiment, the efficacy module 264 is configured to determine a patient is more suitable for vagus nerve stimulation therapy in response to the resting heart rate of the patient being greater than the resting heart rate threshold. In one embodiment, the resting heart rate threshold is approximately seventy beats per minute. In other embodiments, the resting heart rate threshold is greater than or less than seventy beats per minute (e.g., 55, 60, 65, 75, 85, etc.). In an alternative embodiment, the efficacy module 264 is configured to compare the resting heart rate of the patient to a resting heart rate range (e.g., a minimum resting heart rate of 55, 60, 65, 70, etc.; a maximum resting heart rate of 60, 65, 70, 75, 80, 85, etc.). The efficacy module 264 may be further configured to assign a first value or first classification to patients that satisfy the resting heart rate threshold and/or the resting heart rate range, and assign a second value or second classification to patients that do not satisfy the resting heart rate threshold and/or the resting heart rate range. The first value or first classification may include a greater weight than the second value or second classification (e.g., for use with the combination of other characteristics when determining a composite weighted score). Alternatively, the efficacy module 264 may assign a value from a range of values based on the patient's resting heart rate relative the resting heart rate threshold and/or the resting heart rate range.

In some embodiments, the efficacy module 264 is configured to compare a nocturnal heart rate (e.g., a sleeping heart rate, etc.) of the patient to a nocturnal heart rate threshold. By way of example, patients with a high nocturnal heart rate and non-dipping of heart rate may be associated with increased risk of cardiovascular disease and all-cause mortality. According to an exemplary embodiment, the efficacy module 264 is configured to determine a patient is more suitable for vagus nerve stimulation therapy in response to the nocturnal heart rate of the patient being greater than the nocturnal heart rate threshold. In one embodiment, the nocturnal heart rate threshold is approximately fifty-five beats per minute. In other embodiments, the resting heart rate threshold is greater than or less than fifty-five beats per minute (e.g., 45, 50, 60, 65, 70, 75, etc.). In an alternative embodiment, the efficacy module 264 is configured to compare the resting heart rate of the patient to a resting heart rate range (e.g., a minimum resting heart rate of 45, 50, 55, etc.; a maximum resting heart rate of 50, 55, 60, 65, 70, 75, etc.). The efficacy module 264 may be further configured to assign a first value or first classification to patients that satisfy the nocturnal heart rate threshold and/or the nocturnal heart rate range, and assign a second value or second classification to patients that do not satisfy the nocturnal heart rate threshold and/or the nocturnal heart rate range. The first value or first classification may include a greater weight than the second value or second classification (e.g., for use with the combination of other characteristics when determining a composite weighted score). Alternatively, the efficacy module 264 may assign a value from a range of values based on the patient's nocturnal heart rate relative the nocturnal heart rate threshold and/or the nocturnal heart rate range.

In some embodiments, the efficacy module 264 is configured to determine a heart failure etiology of the patient including an indication of ischemic heart failure or non-ischemic heart failure. By way of example, patients with non-ischemic heart failure may not respond as well to ART as patients with ischemic heart failure. Thus, a first patient may be less suitable for vagus nerve stimulation therapy in response to the first patient having non-ischemic heart failure, while a second patient maybe more suitable for the vagus nerve stimulation therapy in response to the second patient having ischemic heart failure. According to an exemplary embodiment, the efficacy module 264 is configured to determine a patient is more suitable for vagus nerve stimulation therapy in response to the patient at least one of (i) having ischemic heart failure and (ii) not having non-ischemic heart failure. The efficacy module 264 may be further configured to assign a first value or first classification to patients that do not have non-ischemic heart failure (e.g., have ischemic heart failure, have neither), and assign a second value or second classification to patients that do have non-ischemic heart failure. The first value or first classification may include a greater weight than the second value or second classification (e.g., for use with the combination of other characteristics when determining a composite weighted score).

In some embodiments, the efficacy module 264 is configured to determine whether a patient is undergoing existing CRT. By way of example, patients with existing CRT may not respond as well to ART as patient without CRT. Thus, a first patient may be less suitable for vagus nerve stimulation therapy in response to the first patient having existing CRT, while a second patient maybe more suitable for the vagus nerve stimulation therapy in response to the second patient not having CRT. According to an exemplary embodiment, the efficacy module 264 is configured to determine a patient is more suitable for vagus nerve stimulation therapy in response to the patient not having existing CRT. The efficacy module 264 may be further configured to assign a first value or first classification to patients that do not have existing CRT, and assign a second value or second classification to patients that do have existing CRT. The first value or first classification may include a greater weight than the second value or second classification (e.g., for use with the combination of other characteristics when determining a composite weighted score).

In some embodiments, the efficacy module 264 is configured to compare a BNP level and/or the n-terminal of the prohormone BNP (NT-proBNP) to a BNP threshold. By way of example, patients with worse heart failure, as indicated by high BNP levels, may respond better to ART. For example, BNP levels below 100 pg/mL may indicate no heart failure, BNP levels between 100-300 pg/mL may indicate heart failure is present, BNP levels above 300 pg/mL may indicate mild heart failure, BNP levels above 600 pg/mL may indicate moderate heart failure, and BNP levels above 900 pg/mL may indicate severe heart failure. According to an exemplary embodiment, the efficacy module 264 is configured to determine a patient is more suitable for the vagus nerve stimulation therapy in response to the BNP level of the patient being greater than the BNP threshold. In one embodiment, the BNP threshold is approximately 100 pg/mL. In other embodiments, the BNP threshold is greater than or less than 100 pg/mL (e.g., 90 pg/mL, 150 pg/mL, 300 pg/mL, etc.). The efficacy module 264 may be further configured to assign a first value or first classification to patients that satisfy the BNP threshold, and assign a second value or second classification to patients that do not satisfy the BNP threshold. The first value or first classification may include a greater weight than the second value or second classification (e.g., for use with the combination of other characteristics when determining a composite weighted score). Alternatively, the efficacy module 264 may assign a value from a range of values based on the patient's BNP level relative the BNP threshold (e.g., a lower value for a BNP level closer to the BNP threshold, a higher value for a BNP value further from the BNP threshold, etc.).

In some embodiments, the efficacy module 264 is configured to compare a left ventricular EF of the patient to an EF threshold and/or an EF range. By way of example, a low left ventricular EF may indicate that a patient may have heart failure and may respond better to ART. However, too low of a left ventricular EF may indicate the heart disease may be too advanced and the response to ART may be minimal. According to an exemplary embodiment, the efficacy module 264 is configured to determine a patient is more suitable for vagus nerve stimulation therapy in response to the left ventricular EF of the patient being less than a maximum EF threshold. In one embodiment, the maximum EF threshold is 55%. In other embodiments, the maximum EF threshold is 40%. In still other embodiments, the maximum EF threshold is less than 40% (e.g., 35%, 30%, etc.). According to another exemplary embodiment, the efficacy module 264 is configured to determine a patient is more suitable for vagus nerve stimulation therapy in response to the left ventricular EF of the patient being greater than a minimum EF threshold. In one embodiment, the minimum EF threshold is 15%. In other embodiments, the minimum EF threshold is 20%. In still other embodiments, the minimum EF threshold is greater than 20% (e.g., 25%, 30%, etc.). According to still another exemplary embodiment, the efficacy module 264 is configured to determine a patient is more suitable for vagus nerve stimulation therapy in response to the left ventricular EF of the patient being within the EF range (e.g., the minimum EF of the EF range may be 15%, 20%, 25%, etc.; the maximum EF of the EF range maybe 30%, 35%, 40%, 55%, etc.). The efficacy module 264 may be further configured to assign a first value or first classification to patients that satisfy the maximum EF threshold, the minimum EF threshold, and/or the EF range, and assign a second value or second classification to patients that do not satisfy the maximum EF threshold, the minimum EF threshold, and/or the EF range. The first value or first classification may include a greater weight than the second value or second classification (e.g., for use with the combination of other characteristics when determining a composite weighted score). Alternatively, the efficacy module 264 may assign a value from a range of values based on the patient's left ventricular EF relative the minimum EF threshold, the maximum EF threshold, and/or the EF range (e.g., a higher value for a left ventricular EF closer to the maximum EF threshold, a lower value for a left ventricular EF closer to the minimum EF threshold, etc.).

In some embodiments, the efficacy module 264 is configured to compare a HRV of the patient to a HRV threshold. By way of example, patients with a lower HRV may respond better to ART, which increases HRV in heart failure. HRV may be measured using a variety of time-domain measures (e.g., AVNN, SDNN, SDANN, SDNNIDX, rMSSD, pNN50, etc.) and/or frequency-domain measures (e.g., VLF, LF, HF, LF/HF, etc.). According to an exemplary embodiment, the efficacy module 264 is configured to determine a patient is more suitable for vagus nerve stimulation therapy in response to the HRV of the patient being less than the HRV threshold. The efficacy module 264 may be further configured to assign a first value or first classification to patients that satisfy the HRV threshold, and assign a second value or second classification to patients that do not satisfy the HRV threshold. The first value or first classification may include a greater weight than the second value or second classification (e.g., for use with the combination of other characteristics when determining a composite weighted score). Alternatively, the efficacy module 264 may assign a value from a range of values based on the patient's HRV relative the HRV threshold (e.g., a higher value for a HRV closer to the HRV threshold, a lower value for a HRV further from the HRV threshold, etc.)

In some embodiments, the efficacy module 264 is configured to determine whether a patient has autonomic dysfunction. Autonomic dysfunction may be measured using baroreflex sensitivity (BRS), muscle sympathetic nerve activity (MSNA), and/or blood biomarkers (e.g., norepinephrine, acetylcholine, etc.). By way of example, patients with autonomic dysfunction may respond better to ART, which restores autonomic balance. Thus, a first patient may be more suitable for vagus nerve stimulation therapy in response to the first patient having autonomic dysfunction, while a second patient may be less suitable for the vagus nerve stimulation therapy in response to the second patient not having autonomic dysfunction. According to an exemplary embodiment, the efficacy module 264 is configured to determine a patient is more suitable for vagus nerve stimulation therapy in response to the patient having autonomic dysfunction. The efficacy module 264 may be further configured to assign a first value or first classification to patients that do have autonomic dysfunction, and assign a second value or second classification to patients that do have autonomic dysfunction. The first value or first classification may include a greater weight than the second value or second classification (e.g., for use with the combination of other characteristics when determining a composite weighted score).

In some embodiments, the efficacy module 264 is configured to compare an indication of a level and/or an amount of inflammation to an inflammation threshold. Inflammation may be measured using blood biomarkers such as C-reactive protein (CRP), interleukin (IL)-1, IL-6, IL-8, monocyte chemoattractant protein-1 (MCP-1), matrix metalloproteinases (MMPs), etc. By way of example, patients with higher levels of inflammation may respond better to ART, which has anti-inflammatory effects. According to an exemplary embodiment, the efficacy module 264 is configured to determine a patient is more suitable for the vagus nerve stimulation therapy in response to the level of inflammation of the patient being greater than the inflammation threshold. The efficacy module 264 may be further configured to assign a first value or first classification to patients that satisfy the inflammation threshold, and assign a second value or second classification to patients that do not satisfy the inflammation threshold. The first value or first classification may include a greater weight than the second value or second classification (e.g., for use with the combination of other characteristics when determining a composite weighted score). Alternatively, the efficacy module 264 may assign a value from a range of values based on the patient's level of inflammation relative the inflammation threshold (e.g., a lower value for a level of inflammation closer to the inflammation threshold, a higher value for a level of inflammation further from the inflammation threshold, etc.)

The efficacy module 264 may be further configured to determine a metric of a patient's suitability for receiving the vagus nerve stimulation based on the comparison of the one or more physiological characteristics of the patient and the one or more criteria (e.g., the potential efficacy of VNS and/or eVNS). In one embodiment, the efficacy module 264 is configured to determine a composite score for the patient based on the one or more physiological characteristics of the patient relative to the one or more criteria (e.g., the aggregation or other compilation of the first values/first classification, the second values/second classifications, and/or the values from the ranges of values). In some embodiments, the one or more physiological characteristics are weighted (e.g., such that some characteristics carry more weight than others, some are more important or influential in assessing a patient, etc.) such that the efficacy module 264 determines a weighted composite score for a patient. According to an exemplary embodiment, the efficacy module 264 is configured to generate the composite score using a weighted combination of multiple suitability metrics. Each suitability metric may be generated based on a respective characteristic relative to an associated criteria where the composite score is generated by applying a weight to each metric. In some embodiments, the weights are applied to the values for each respective physiological characteristic of the patient (e.g., the first values/classification, the second values/classifications, the values from the ranges of values, etc.) to determine the weighted composite score. Such a process of applying values to the characteristics may allow for the normalization of the characteristics so that each may be combined to determine the composite score.

In some embodiments, the efficacy module 264 is configured to compare one or more characteristics of the patient to one or more criteria and classify the patient as a member of one of multiple patient classes. For example, in some embodiments, a value associated with one or more characteristics (e.g., a weighted composite score) may be compared to an efficacy mapping (e.g., rating system, rating guidelines, etc.), such as one or more thresholds of one or more criteria, to classify a patient as one of a plurality of patient classes using the result of the comparison. Each patient class may be associated with a different level of suitability for receiving vagus nerve stimulation therapy. In one embodiment, the efficacy mapping includes a single threshold. By way of example, characteristics values (e.g., composite scores) that satisfy the single threshold (e.g., greater than, etc.) may indicate patients that are in a first patient class that includes patients considered likely to be good candidates (e.g., suitable) to have a vagus nerve stimulator implanted to provide VNS and/or eVNS (e.g., candidates for whom VNS and/or eVNS is likely to be successful, or result in improvement of the patient's condition), while composite scores that do not satisfy the single threshold (e.g., less than, etc.) may indicate patients that are in a second patient class that includes patients likely to be bad candidates (e.g., not suitable) to have a vagus nerve stimulator implanted to provide VNS and/or eVNS (e.g., candidates for whom VNS and/or eVNS is unlikely to be successful, or result in no substantial improvement or in degradation of the patient's condition). In another embodiment, the efficacy mapping includes two threshold values, a first threshold value and a second threshold value less than the first threshold value. By way of example, characteristic values (e.g., composite scores) that satisfy the first threshold (e.g., greater than, etc.) may indicate patients that are in the first class or good candidates (e.g., suitable) to have a vagus nerve stimulator implanted to provide VNS and/or eVNS, characteristic values that satisfy the second threshold (e.g., less than, etc.) may indicate patients that are in the second class or bad candidates (e.g., not suitable) to have a vagus nerve stimulator implanted to provide VNS and/or eVNS, and characteristic values that satisfy neither the first and second thresholds (e.g., lie between the first and second thresholds, etc.) are in a third class that indicates that VNS and/or eVNS may or may not be effective on the patient (e.g., up to a physician's judgment, a potential candidate, etc.). For example, characteristic values that do not satisfy the first threshold, but are closer to the first threshold than the second threshold, may indicate a greater likelihood that implanting a vagus nerve stimulator to provide VNS and/or eVNS will be successful. In another example, characteristic values that do not satisfy the first threshold, but are closer to the second threshold that the first threshold, may indicate a lesser likelihood that implanting a vagus nerve stimulator to provide VNS and/or eVNS will be successful. In other embodiments, the efficacy mapping includes a plurality of thresholds to correspond with various possible composite scores (e.g., a first threshold indicating 95% potential success, a second threshold indicating 80% potential success, a third threshold indicating 70% potential success, a fourth threshold indicating 60% potential success, a fifth threshold indicating 50% potential success, etc.).

The efficacy module 264 may be further configured to provide an indication of the patient's suitability for receiving the vagus nerve stimulation therapy via the user I/O device 210. In one embodiment, the indication includes the composite and/or the weighted composite score. In other embodiments, the indication includes a percentage, a value, and/or another metric indicative of the potential (e.g., predicted, etc.) efficacy of the vagus nerve stimulation therapy on the patient based on the weighted and/or composite score. In other embodiments, the indication includes a recommendation (e.g., "pass," "fail," "approved," "do not provide VNS treatment," etc.) regarding whether the patient should have a vagus nerve stimulator (e.g., the vagus nerve stimulator 10, etc.) implanted based on the weighted and/or composite score.

According to another exemplary embodiment, the efficacy module 264 is configured to use the weighted and/or composite score as a precursor determination to whether stimulation testing and analysis should be performed by the operator of the VNS analysis system 200 on a patient. In some embodiments, the response of the patient to the stimulation testing and the one or more characteristics of the patient are cooperatively used to determine a patient's suitability for receiving vagus nerve stimulation therapy. In other embodiments, the response of the patient to the stimulation testing is used independent (e.g., alternatively, for verification purposes, etc.) of the one or more physiological characteristics of the patient. Thus, the patient's suitability for receiving the vagus nerve stimulation therapy may be determined based on the one or more physiological characteristics of the patient, the response of the patient to the stimulation testing, or a combination thereof (e.g., the weighted and/or composite score is based on the physiological characteristics and/or the physiological response of a patient).

Referring back to FIG. 5, the stimulation module 260 may be configured to control operation of the stimulation device 220 (e.g., the electrodes 38, etc.) to provide stimulation to the vagus nerve of a patient. The stimulation module 260 may be further configured to monitor and/or control stimulation parameters and/or levels provided by the stimulation device 220 (e.g., current, voltage, power, signal frequency, pulse width, signal ON time, signal OFF time, etc.). In some embodiments, the stimulation module 260 is configured to control the stimulation device 220 according to a predefined stimulation protocol. In other embodiments, the stimulation module 260 is configured to control the stimulation device 220 based on manually input control parameters provided by an operator of the VNS analysis system 200.

The stimulation analysis module 262 may be configured to receive response data acquired by the sensors 230 indicative of a physiological response of the patient to the stimulation of the vagus nerve. Therefore, the stimulation analysis module 262 may be configured to monitor one or more physiological responses of the patient to the stimulation including heart rate changes, HRV changes, breathing pattern changes, induced pain, and/or blood pressure changes, among other possible responses induced by the stimulation. As shown in FIG. 5, the stimulation analysis module 262 is communicably coupled to the efficacy module 264. Thus, the stimulation analysis module 262 may provide information regarding the physiological response of a patient to the efficacy module 264 to perform further analysis.

The efficacy module 264 may be configured to receive and store one or more response criteria (e.g., screening parameters, etc.) regarding a patient's suitability for receiving vagus nerve stimulation therapy. The one or more response criteria may be predefined within the efficacy module 264 and/or manually input by an operator of the VNS analysis system 200. The one or more response criteria may include a heart rate change threshold or a heart rate variability threshold, among other possibilities. The thresholds may be a magnitude difference and/or a percentage difference (e.g., of a post-stimulation value relative to a pre-stimulation value, etc.). The efficacy module 264 may thereby be configured to receive the information regarding the physiological response of a respective patient to the provided stimulation (e.g., from the stimulation analysis module 262, etc.). The efficacy module 264 may further determine the patient's suitability for receiving vagus nerve stimulation therapy based on the one or more response criteria and the one or more physiological responses of the patient being assessed for vagus nerve stimulation therapy. For example, if the heart rate of a patient changes more than the heart rate change threshold (e.g., in response to the stimulation, etc.), the patient may be suitable to receive vagus nerve stimulation therapy.

The efficacy module 264 may be further configured to determine the patient's suitability for receiving the vagus nerve stimulation therapy based on the one or more response criteria and the physiological response of the patient to the stimulation. As described above, the efficacy module 264 may determine the patient's suitability for receiving the vagus nerve stimulation therapy (e.g., the weighted and/or composite score, etc.) based on (i) the comparison of the one or more characteristics to the one or more criteria, (ii) the comparison of the physiological response to the one or more response criteria, or both (i) and (ii).

Figure 6:
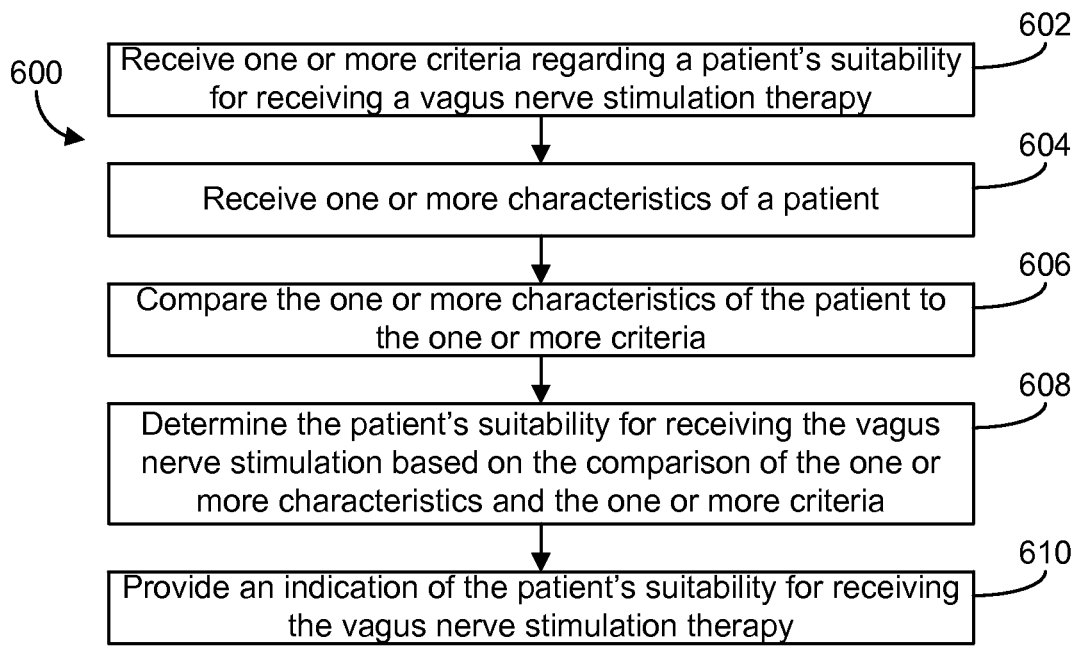
FIG. 6 is a flow diagram of a method for assessing a patient's suitability for receiving a vagus nerve stimulation therapy, according to an exemplary embodiment.

Referring now to FIG. 6, a method 600 for assessing a patient's suitability for receiving a vagus nerve stimulation therapy is shown according to an exemplary embodiment. In one example embodiment, method 600 may be implemented with the VNS analysis system 200 of FIG. 5. Accordingly, method 600 may be described in regard to FIG. 5.

At step 602, the VNS analysis system 200 is configured to receive one or more criteria regarding a patient's suitability for receiving a vagus nerve stimulation therapy. In one embodiment, the one or more criteria are manually input by an operator via an input device (e.g., the user I/O device 210, etc.). In other embodiments, the one or more criteria are predefined within the memory (e.g., the memory 256, etc.) of the VNS analysis system 200. According to an exemplary embodiment, the one or more criteria include an age range or threshold, a resting heart rate threshold, a nocturnal heart rate threshold, ischemic heart failure versus non-ischemic heart failure, existing cardiac resynchronization therapy, a brain natriuretic peptide threshold, a left ventricular ejection fraction range or threshold, a heart rate variability threshold, autonomic dysfunction, and/or an inflammation threshold.

At step 604, the VNS analysis system 200 is configured to receive one or more characteristics (e.g., physiological characteristics, etc.) of a patient. According to an exemplary embodiment, the one or more characteristics of the patient are determined and/or measured using non-invasive methods. In some embodiments, at least a portion of the one or more characteristics of the patient are manually input by the operator via the input device (e.g., the one or more characteristics were determined prior to the assessment, etc.). In some embodiments, at least a portion of the one or more characteristics of the patient are received from one or more sensors or external devices (e.g., acquired by the sensors 230, downloaded from a patient file on a remote server or database, etc.). According to an exemplary embodiment, the one or more characteristics include an indication of autonomic dysfunction, heart rate variability, an inflammation amount, a left ventricular ejection fraction, a brain natriuretic peptide level, existing cardiac resynchronization therapy, heart failure etiology (e.g., ischemic heart failure versus non-ischemic heart failure, etc.), a resting heart rate, a nocturnal heart rate, and/or an age of the patient.

At step 606, the VNS analysis system 200 is configured to compare the one or more characteristics of the patient to the one or more criteria. At step 608, the VNS analysis system 200 is configured to determine the patient's suitability for receiving the vagus nerve stimulation based on the comparison of the one or more characteristics of the patient and the one or more criteria. In one embodiment, the VNS analysis system 200 is configured to determine a composite score for the patient based on each of the characteristics relative to the respective criteria. In some embodiments, the VNS analysis system 200 is configured to determine a weighted composite score for the patient based on each of the characteristics relative to the respective criteria.

At step 610, the VNS analysis system 200 is configured to provide an indication on an output device (e.g., the user I/O device 210, etc.) that indicates the patient's suitability for receiving the vagus nerve stimulation therapy (e.g., the potential efficacy of VNS, etc.). In some embodiments, the indication includes the weighted and/or composite score. In some embodiments, the indication includes a percentage, a value, and/or another metric indicative of the potential (e.g., predicted, etc.) efficacy of the vagus nerve stimulation therapy on the patient (e.g., determined by the VNS analysis system 200 using the weighted and/or composite score, etc.). In other embodiments, the indication includes a recommendation (e.g., "pass," "fail," "approved," "do not provide VNS treatment," etc.) regarding whether the patient should have a vagus nerve stimulator (e.g., the vagus nerve stimulator 10, etc.) implanted (e.g., based on the weighted and/or composite score, etc.).

Figure 7:
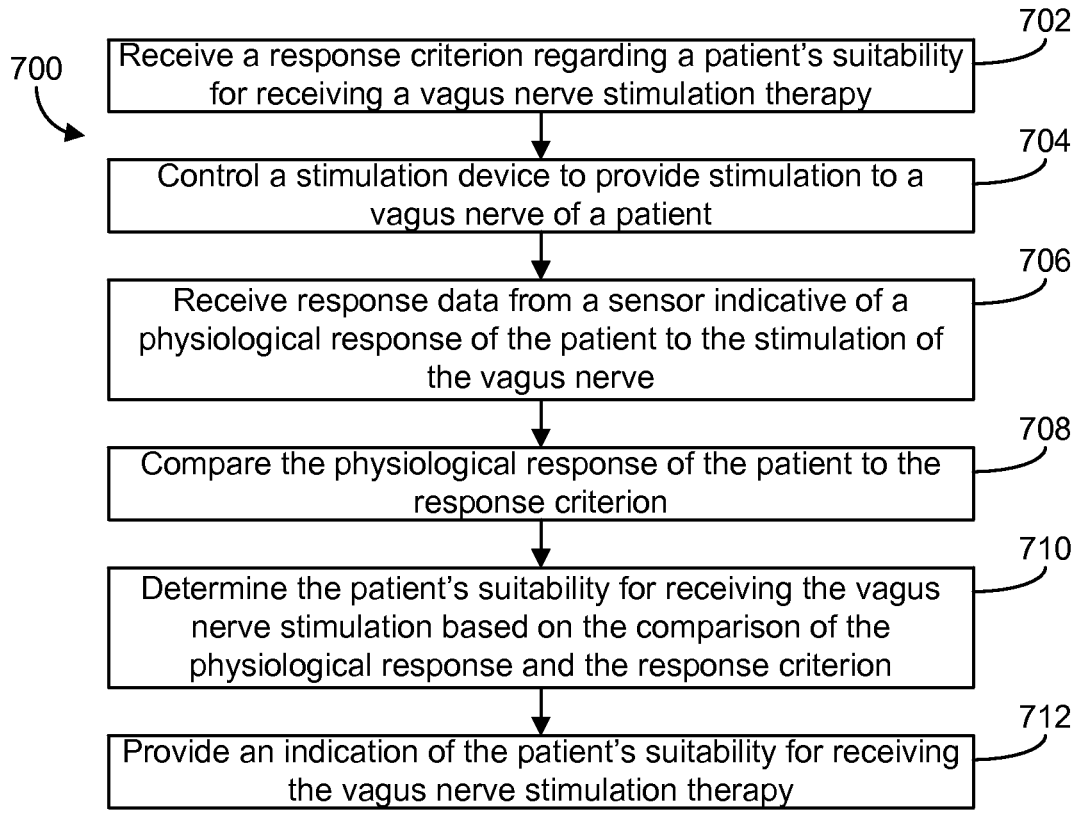
FIG. 7 is a flow diagram of a method for assessing a patient's suitability for receiving a vagus nerve stimulation therapy, according to another exemplary embodiment.

Referring now to FIG. 7, a method 700 for assessing a patient's suitability for receiving a vagus nerve stimulation therapy is shown according to another exemplary embodiment. In one example embodiment, method 700 may be implemented with the VNS analysis system 200 of FIG. 5. Accordingly, method 700 may be described in regard to FIG. 5.

At step 702, the VNS analysis system 200 is configured to receive a response criterion regarding a patient's suitability for receiving a vagus nerve stimulation therapy. In one embodiment, the response criterion is manually input by an operator via an input device (e.g., the user I/O device 210, etc.). In other embodiments, the response criterion is predefined within the memory (e.g., the memory 256, etc.) of the VNS analysis system 200. According to an exemplary embodiment, the response criterion includes a response of a heart rate of the patient (e.g., a change in the heart rate, heart rate variability, a minimum change in heart rate, a maximum change in heart rate, a percent change in heart rate, etc.) due to stimulation (e.g., to the vagus nerve, etc.).

At step 704, the VNS analysis system 200 is configured to control operation of a stimulation device (e.g., the stimulation device 220, etc.) to provide stimulation to a vagus nerve of a patient (e.g., eVNS, direct VNS, auricular VNS, acute stimulation, etc.). According to an exemplary embodiment, the VNS analysis system 200 is configured to control operation of the stimulation device according to a predefined stimulation protocol. In one embodiment, the stimulation device includes a lead (e.g., the lead 30, etc.) having at least one electrode (e.g., the electrodes 38, etc.) endovascularly positioned within a lumen of a vein (e.g., the azygos vein, etc.) proximate a portion of the vagus nerve (e.g., the cardiac fascicles that branch from the vagus nerve, etc.). Thereby, the stimulation device may provide the stimulation transvacularly through a wall of the vein to the vagus nerve. In another embodiment, the stimulation device includes an external stimulation device positioned outside the body of the patient to provide the stimulation to through the skin of the patient. In one embodiment, the external stimulation device includes an auricular stimulation device configured to provide auricular stimulation around an ear of the patient. In other embodiments, the external stimulation device includes another type of stimulation device configured to provide stimulation to another external area of the patient (e.g., the chest, the back, the neck, etc.). In still other embodiments, the stimulation device includes a cuff-type electrode (e.g., the cuff-type electrode 40, etc.) or other type of electrode temporarily implanted onto the vagus nerve and configured to provide stimulation directly to the vagus nerve. By way of example, such an invasive VNS testing method may be used while a patient is already undergoing a surgical procedure that facilitates accessing the vagus nerve (e.g., the reason for performing the surgical procedure is not performed to facilitate the testing, an additional step included in another procedure, etc.).

At step 706, the VNS analysis system 200 is configured to receive response data from a sensor (e.g., the sensors 230, etc.) indicative of a physiological response of the patient to the stimulation of the vagus nerve (e.g., endovascular, external, and/or direct stimulation to the vagus nerve, etc.). The physiological response may include a heart rate, a change in the heart rate, heart rate variability, and/or other physiological responses of the patient induced by the stimulation.

At step 708, the VNS analysis system 200 is configured to compare the physiological response of the patient to the response criterion. At step 710, the VNS analysis system 200 is configured to determine the patient's suitability for receiving the vagus nerve stimulation based on the comparison of the physiological response of the patient and the response criterion. At step 712, the VNS analysis system 200 is configured to provide an indication on an output device (e.g., the user I/O device 210, etc.) that indicates the patient's suitability for receiving the vagus nerve stimulation therapy.

In some embodiments, the indication includes a percentage, value, and/or other metric indicative of the potential (e.g., predicted, etc.) efficacy of the vagus nerve stimulation therapy on the patient (e.g., determined by the VNS analysis system 200 based on the physiological response, etc.). In other embodiments, the indication includes a recommendation (e.g., "pass," "fail," "approved," "do not provide VNS treatment," etc.) regarding whether the patient should have a vagus nerve stimulator (e.g., the vagus nerve stimulator 10, etc.) implanted (e.g., based on the physiological response, etc.).

In some embodiments, method 600 and method 700 are combined. By way of example, the VNS analysis system 200 may determine the patient's suitability for receiving the vagus nerve stimulation therapy based on both (i) the comparison of the one or more characteristics to the one or more criteria and (ii) the comparison of the physiological response to the response criterion. In one embodiment, the VNS analysis system 200 is configured to determine a composite score for the patient based on each of the characteristics and the physiological response relative to the respective criteria. In some embodiments, the VNS analysis system 200 is configured to determine a weighted composite score for the patient based on each of the characteristics and the physiological response relative to the respective criteria. In an alternative embodiment, the VNS analysis system 200 implements method 600 first to determine whether it is worthwhile (e.g., necessary, etc.) to perform any stimulation testing (i.e., method 700, etc.).

In view of the above, it can be appreciated that eVNS presents a less invasive or minimally-invasive device, system, and method for delivering stimulation energy to the vagus nerve, as compared to a fully-implanted VNS neurostimulator coupled to an electrode that is in direct contact with the vagus nerve. As can also be appreciated, the eVNS approach may be used to evaluate the patient's response to vagus nerve stimulation so as to generate data useful in determining whether the candidate is an appropriate candidate for a longer term of VNS therapy. As seen with, for example, the CardioFit® system sold by BioControl Medical, a fully-implanted system is provided that requires the patient to endure the implantation surgery and a titration period before learning whether the patient is a suitable candidate for the therapy. Accordingly, it is desirable to provide a system, such as an eVNS system, that allows a physician to evaluate the patient's response to VNS therapy prior to committing to a fully-implanted system. Furthermore, it is desirable to provide a system, such as an eVNS system, that allows a physician to obtain response data from the patient to identify any negative effects from the VNS therapy.

With further reference to the CardioFit® system sold by BioControl Medical, the INOVATE-HF study (ClinicalTrials.gov Identifier: NCT01303718) under which the CardioFit® system was evaluated set forth a number of factors or criteria that was used to determine whether the patient is a suitable candidate for the therapy. Specifically, the inclusion criteria for the CardioFit® system in the INOVATE-HF study is:

1. Chronic symptomatic heart failure in New York Heart Association functional class III.
2. Age of at least 18 years.
3. Subjects should be predominately in sinus rhythm at the time of enrollment.
4. On stable optimally uptitrated medical therapy recommended according to current guidelines as standard of care for heart failure therapy.
5. LVEF ≤40% per site measurement within three months before enrollment.
6. The left ventricular end diastolic diameter, per site measurement, should be between 50 and 80 mm.
7. The subject is a male or postmenopausal female. Females of childbearing age may be included if an acceptable contraception measure is used.
8. Subject must sign an approved informed consent form. Subject agrees to attend all followup evaluations.
9. Subjects with CRT devices may be included in the trial provided they have had CRT for at least 12 months.

The exclusion criteria for the CardioFit® system in the INOVATE-HF study is:

1. Presence of a life threatening condition or disease other than heart failure, that is likely to lead to death within 6 months.
2. Acute myocardial infarction (MI), variant angina pectoris, unstable angina or acute coronary syndrome in the previous one month.
3. History of stroke or TIA within the previous 3 months or significant neurological damage that would impair the ability to respond to or detect improvement with the vagal nerve stimulation.
4. Coronary Artery Bypass Surgery (CABG), valve replacement or repair, aortic surgery or PCI) in the prior 3 months or planned/anticipated within 6 months.
5. Heart failure due to acute myocarditis, restrictive cardiomyopathy, constrictive pericarditis or hemodynamically significant aortic valve insufficiency, aortic stenosis, or mitral valve stenosis.
6. Severe renal failure (creatinine level >3 mg/dL (265 micromole/liter)).
7. Severe hepatic failure (transaminase level four times ULN, or total bilirubin level >1.8 mmol/dL).
8. Uncontrolled Diabetes Mellitus, which in the opinion of the investigator, would compromise the safety of the implant procedure and/or the ability to respond or detect improvement with vagal nerve stimulation.
9. Previous right neck surgery, including for cerebrovascular disease (CVD), malignancy, and previous irradiation therapy of the neck, which in the opinion of the implanting surgeon, would preclude safe implantation of the vagal nerve cuff. Subjects with more than 70% right carotid artery stenosis assessed on carotid ultrasound are excluded.
10. Current hypotension (systolic blood pressure below 80 mmHg).
11. Active peptic ulcer disease or history of upper GI bleeding, or ulcer within 6 months.
12. History of lung disease such as severe asthma, COPD (e.g., FEV1<1.5 liter) or continuous oxygen dependence.
13. 2nd or 3rd degree AV block or other pacemaker indication that is not treated with a pacemaker.
14. Chronic atrial fibrillation or flutter in the previous 3 months, or hospitalization for AF due to clinical manifestations of such in the last 6 months.
15. Use of unipolar sensing
16. Congenital or acquired long QT syndrome.
17. Documented recorded or suspected vaso-vagal syncope or vaso depressor syncope.
18. Treatment by investigational drug or device within the past 3 months.
19. The subject must not have received inotropic therapy within 2 months or be considered a possible candidate for inotropic therapy within the next 1 month.

20. Inability to understand the informed consent and/or prior diagnosis of major affective disorder e.g., major depression or bipolar disorder or schizophrenia that requires ongoing treatment and is not adequately controlled by medication.
21. Subjects transplanted with heart or other tissues or organs, or on a heart transplant waiting list and anticipated to receive a transplant within 6 months of randomization.
22. Immunosuppressed subjects; subjects under systemic steroid treatment.
23. Anemia with Hgb ≤9.5 g/L. Treatment with erythropoietin or other similar agents is allowed if used to keep Hgb >9.5 g/L.
24. Untreated obstructive sleep apnea ("OSA") with apnea-hypopnea index of 15 or more; or OSA that is treated for less than 3-months.

As can be appreciated from the above-listed inclusion and exclusion criteria, a patient being considered for an implantation of the CardioFit® system is evaluated by a number of criteria that do not directly measure or evaluate the patient's response to vagus nerve stimulation. Furthermore, the inclusion and exclusion criteria for the CardioFit® system study is limited to factors that are obtained from known methods that do not directly evaluate the reaction of the patient to VNS stimulation, and that do not present information that clearly identifies patients that are not suitable for implantation with the CardioFit® system.

It is believed that the inclusion and exclusion criteria used by others when evaluating a patient's suitability for VNS therapy can be enhanced when considering additional criteria. For example, those additional criteria can include:

1. An evaluation of an autonomic dysfunction status of the patient. It is believed that patients with autonomic dysfunction may respond better to ART, which restores autonomic balance. Autonomic dysfunction can be measured using baroreflex sensitivity (BRS), muscle sympathetic nerve activity (MSNA), or blood biomarkers (norepinephrine, acetylcholine, etc.).
2. An evaluation of a heart rate variability (HRV) status of the patient. It is believed that patients with lower HRV may respond better to ART, which increases HRV in heart failure. HRV can be measured using a variety of time-domain measures (AVNN, SDNN, SDANN, SDNNIDX, rMSSD, pNN50) and frequency domain measures (VLF, LF, HF, LF/HF).
3. An evaluation of an inflammation status of the patient. It is believed that patients with higher levels of inflammation may respond better to ART, which has anti-inflammatory effects. Inflammation can be measured using blood biomarkers such as C-reactive protein (CRP), interleukin (IL)-1, IL-6, IL-8, monocyte chemoattractant protein-1 (MCP-1), and matrix metalloproteinases (MMPs).
4. An evaluation of an ejection fraction (EF) status of the patient. It is believed that patients with lower left ventricular ejection fraction may respond better to ART. This cutoff may be at EF<40%, EF<35%, or EF<30%.
5. An evaluation of an EF range status of the patient. It is believed that patients with low left ventricular ejection fraction may respond better to ART; however, if EF is too low, the disease may be too advanced, and response may be worse. The EF range may be less than 30%, 35%, or 40%, and more than 15%, 20%, or 25%.
6. An evaluation of a brain natriuretic peptide (BNP) status of the patient. It is believed that patients with worse heart failure, as indicated by high BNP or the n-terminal of the prohormone BNP (NT-proBNP) may respond better to ART.
7. An evaluation of a cardiac resynchronization therapy (CRT) status of the patient. It is believed that some patients with existing CRT do not respond as well to ART as patients without CRT.
8. An evaluation of a heart failure etiology status of the patient. It is believed that some patients with non-ischemic heart failure do not respond as well to ART as patients with ischemic heart failure.
9. An evaluation of a resting heart rate status of the patient. It is believed that patients with high resting heart rate despite OMT may be under high sympathetic drive and may thus be more sensitive to vagal stimulation based on the accentuated antagonism mechanism. High HR may be defined as HR>70 bpm.
10. An evaluation of a nocturnal heart rate of the patient. It is believed that a high nocturnal HR may be another target for screening since in limited clinical experience increased sleep heart rate and non-dipping of heart rate were associated with increased risk of CVD and all-cause mortality, but awake heart rate was not.
11. An evaluation of the patient's age. It is believed that age could be used as a screening parameters since signal conduction on nerves and brain plasticity, altered with age, could prevent VNS efficacy.
12. An evaluation of a health index of the patient. It is believed that patients capable of achieving a certain level of physical activity (e.g., able to walk between 150 and 450 meters during a six minute walking test), having a body mass index (BMI) of less than 30-35, having an EF within a suitable EF range, cardiac output within a suitable range, and/or having a diagnosed heart failure condition for less than five to ten years are more suitable to receive vagus nerve stimulation therapy.
13. An evaluation of dyssynchrony of the patient. It is believed that patients with lower dyssynchrony are more suitable to receive vagus nerve stimulation therapy. By way of example, suitable patients may have a low electrical ventricular dyssynchrony. For example, such patients may not be receiving CRT therapy and/or may have a QRS complex less than 150 milliseconds. By way of another example, suitable patients may have a low mechanical ventricular dyssynchrony. For example, the difference between the left ventricular pre-ejection interval (LVPEI) and the right ventricular pre-ejection interval (RVPEI) of a suitable patient may be less than forty milliseconds. In another example, the difference between subsequent LVPEIs of a suitable patient may be less than 140 milliseconds.
14. An evaluation of a potential for improvement of the patient. It is believed that patients with a greater potential for improvement are more suitable to receive vagus nerve stimulation therapy. For example, patients with a high resting heart rate (e.g., greater than 70 bpm, etc.), a low HRV, a low baroreflex sensitivity (e.g., less than 3 ms/mmHg, etc.), and/or a low heart rate recovery (e.g., less than 11 bpm/min, etc.) may be more suitable to receive vagus nerve stimulation therapy.
15. An evaluation of a severity of heart failure of the patient. It is believed that patients within a certain heart failure severity range may be more suitable to receive vagus nerve stimulation therapy. The heart failure severity range may include patients within class II and class III of the New York Heart Association (NYHA) classification of symptoms for heart failure (class I and class IV may or may not be excluded). The heart failure severity range may additionally or alternatively include a duration for which a patient has had a diagnosed heart failure condition (e.g., between zero and five years, less than eight to ten years, etc.) and/or a rate at which the severity is increasing (e.g., a period of time between the change in classification, a change in a measured parameter of a heart failure test including, for example, a change in the distance walked during a six minute walking test, etc.).

16. An evaluation of a composite score of all the above criteria, or a subset of those criteria.

As can be appreciated from the above-listed additional criteria, a patient being considered for an implantation of a VNS system can be evaluated by a number of additional criteria that do not directly measure or evaluate the patient's response to vagus nerve stimulation. As can also be appreciated, one, a few, or all of the above-listed additional criteria can be used with one or more of the criteria used by others when evaluating a patient's suitability for a VNS therapy, such as the criteria associated with the INOVATE-HF study of the CardioFit® system.

In addition to the above criteria, the embodiments described above (and in particular the embodiments describing eVNS devices or methods that can be used to evaluate a patient's response to VNS stimulation) can be used to directly assess the patient's response to a form of vagus nerve stimulation prior to committing to the implantation of a fully-implanted system. The use of an evaluative VNS system, such as eVNS, can provide still additional criteria useful when determining whether a patient is a suitable candidate. Those still additional criteria can include:

1. An evaluation of the patient's heart rate during an acute eVNS procedure. This can include an indication of a heart rate drop when stimulation is applied.
2. An evaluation of the patient's heart rate stability during an acute eVNS procedure. This can include an indication of a heart rate stability change when stimulation is applied.
3. An evaluation of the patient's blood pressure during an acute eVNS procedure. This can include an indication of a blood pressure change when stimulation is applied.
4. An evaluation of the patient's left ventricle diastolic filling time during an acute eVNS procedure. This can include an indication of an increase in the patient's left ventricle diastolic filling time when stimulation is applied.
5. An evaluation of the patient's tolerance to vagus nerve stimulation. This may include an indication of a patient's tolerance to higher current stimulation and/or a patient's lower sensitivity to a rate of titration (e.g., an increase in simulation events over time, an increase in stimulation current over time, etc.). By way of example, patients that are capable of receiving a higher stimulation current (e.g., greater than 3.5 mA, 4 mA, etc.) may have an increased, positive response to vagus nerve stimulation. By way of another example, patients that are more tolerant to an increasing rate of stimulation over a time period and/or to an increasing rate of a stimulation current over a time period may be more suitable to receive vagus nerve stimulation. The patient's susceptibility may be determined during a post-stimulation survey used to indicate a level of discomfort and/or pain induced from such stimulation, a measure of one or more parameters during the stimulation (e.g., a change in heart rate, etc.), and/or an occurrence of one or more physiological side effects (e.g., coughing, loss of voice, discomfort, etc.).

As can also be appreciated, one, a few, or all of the above-listed still additional criteria can be used with one or more of above-listed additional criteria and/or one or more of the criteria used by others when evaluating a patient's suitability for a VNS therapy, such as the criteria associated with the INOVATE-HF study of the CardioFit® system.

The above-listed criteria, which include the additional criteria and the still additional criteria, can be presented to a physician or interested health care provider to instruct on whether the patient is suitable for a VNS therapy. The criteria can be in the form of a website or product labeling, and can be presented as an inclusion or exclusion criteria.

In the embodiments described above, and in particular with regard to the embodiments describing eVNS devices or methods that can be used to evaluate the patients response to VNS stimulation, additional inclusion and exclusion criteria can be identified and evaluated when determining whether a patient is a suitable candidate for vagus nerve stimulation provided by a VNS or eVNS system.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z. Thus, such conjunctive language is not generally intended to imply that certain embodiments require at least one of X, at least one of Y, and at least one of Z to each be present.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for assessing a patient's suitability for implantation of a vagus nerve stimulation (VNS) system, comprising:
    receiving a response criterion regarding the patient's suitability for the implantation of the VNS system, the response criterion being a screening parameter comprising at least one of a heart rate change threshold or a heart rate variability threshold;
    controlling a stimulation device to provide stimulation to a vagus nerve of the patient;
    receiving, from a sensor, response data indicative of a physiological response of the patient to the stimulation of the vagus nerve;
    comparing the response criterion to the physiological response; and
    determining the patient's suitability for the implantation of the VNS system based on the comparison between the response criterion and the physiological response of the patient to the stimulation.

2. The method of claim 1, wherein the stimulation device includes a lead having at least one electrode endovascularly positioned within a lumen of a vein proximate a portion of the vagus nerve, wherein the stimulation device provides the stimulation transvascularly through a wall of the vein.

3. The method of claim 2, wherein the vein includes an azygos vein, and the portion of the vagus nerve includes cardiac fascicles that branch from the vagus nerve.

4. The method of claim 1, wherein the stimulation device includes an external stimulation device positioned outside a body of the patient and provides the stimulation through a skin of the patient.

5. The method of claim 4, wherein the external stimulation device includes an auricular stimulation device configured to provide auricular stimulation around an ear of the patient.

6. A method for assessing a patient's suitability for implantation of a vagus nerve stimulation (VNS) system, comprising:
    receiving a criterion regarding the patient's suitability for the implantation of the VNS system, the criterion being a screening parameter comprising at least one of a resting heart rate threshold, a nocturnal heart rate threshold, an indication of whether the patient has ischemic heart failure, an indication of whether the patient has non-ischemic heart failure, an indication of existing cardiac resynchronization therapy, a brain natriuretic peptide threshold, a left ventricular ejection fraction threshold, a left ventricular ejection fraction range, or a heart rate variability threshold;
    receiving a characteristic of the patient;
    comparing the characteristic to the criterion; and
    classifying the patient as one of a plurality of patient classes using the comparison, wherein each patient class is associated with a different level of the patient's suitability for the implantation of the VNS system.

7. The method of claim 6, further comprising providing, on a display device, an indication of the patient's suitability for the implantation of the VNS system based on the patient class of the patient, the indication indicating whether the patient should receive the implantation of the VNS system.

8. The method of claim 6, wherein comparing the characteristic to the criterion comprises comparing a value of the characteristic to a threshold value of the criterion, and wherein classifying the patient comprises:
    classifying the patient as a member of a first patient class in response to determining the value is greater than the threshold value; and
    classifying the patient as a member of a second patient class in response to determining the value is less than the threshold value.

9. The method of claim 6, wherein comparing the characteristic to the criterion comprises comparing a value of the characteristic to a first threshold and a second threshold of the criterion, wherein the first threshold is greater than the second threshold.

10. The method of claim 9, wherein classifying the patient comprises:
    determining the patient is in a first patient class for which implanting the VNS system to deliver vagus nerve stimulation therapy is likely to be successful in response to determining the value is greater than the first threshold; and
    determining the patient is in a second patient class for which implanting the VNS system to deliver vagus nerve stimulation therapy is unlikely to be successful in response to determining the value is less than the second threshold.

11. The method of claim 10, wherein classifying the patient further comprises determining the patient is in a third patient class in response to determining the value is between the first threshold and the second threshold.

12. The method of claim 9, wherein the characteristic includes a plurality of characteristics, and wherein the criterion includes a plurality of criteria, wherein, in particular, the values for the plurality of characteristics are aggregated to determine a composite score, the first threshold and the second threshold are threshold composite scores, and the patient class of the patient is based on the composite score relative to the first threshold and the second threshold.

13. The method of claim 6, wherein the characteristic is assigned a first value in response to the characteristic satisfying the criterion, and wherein the characteristic is assigned a second value in response to the characteristic not satisfying the criterion.

14. A system for assessing a patient's suitability for implantation of a vagus nerve stimulation (VNS) system, comprising:
    a stimulation device; and
    a computer-readable storage medium having stored thereon instructions, which, when read by a computer, cause the computer to perform the following steps:
        receiving a response criterion regarding the patient's suitability for the implantation of the VNS system, the response criterion being a screening parameter comprising at least one of a heart rate change threshold or a heart rate variability threshold;
        controlling the stimulation device to provide stimulation to a vagus nerve of the patient;

receiving, from a sensor, response data indicative of a physiological response of the patient to the stimulation of the vagus nerve;

comparing the response criterion to the physiological response; and determining the patient's suitability for the implantation of the VNS system based on the comparison between the response criterion and the physiological response of the patient to the stimulation.

15. The system of claim 14, wherein the stimulation device includes a lead having at least one electrode configured to be endovascularly positioned within a lumen of a vein proximate a portion of the vagus nerve, wherein the stimulation device is configured to provide the stimulation transvascularly through a wall of the vein.

16. The system of claim 15, wherein the vein includes an azygos vein, and the portion of the vagus nerve includes cardiac fascicles that branch from the vagus nerve.

17. The system of claim 14, wherein the stimulation device includes an external stimulation device configured to be positioned outside a body of the patient and to provide the stimulation through a skin of the patient.

18. The system of claim 17, wherein the external stimulation device includes an auricular stimulation device configured to provide auricular stimulation around an ear of the patient.

19. The system of claim 14, the computer-readable storage medium having stored thereon further instructions, which, when read by the computer, cause the computer to perform the following steps:

controlling the stimulation device to provide the stimulation according to a predefined stimulation protocol; and/or providing, on a display device, an indication of the patient's suitability for the implantation of the VNS system, the indication indicating whether the patient should receive the implantation of the VNS system;

receiving a characteristic of the patient; and determining the patient's suitability for the implantation of the VNS system based on the response criterion, the physiological response of the patient to the stimulation, and the characteristic of the patient, wherein, in particular, the indication of the patient's suitability includes a composite score based on the physiological response and the characteristic of the patient relative to the response criterion.

20. The system of claim 19, wherein the characteristic is at least one of received or measured using non-invasive methods, and wherein the characteristic includes an indication of at least one of autonomic dysfunction, heart rate variability, inflammation, left ventricular ejection fraction, brain natriuretic peptide, existing cardiac resynchronization therapy, heart failure etiology, resting heart rate, nocturnal heart rate, health index, dyssynchrony, potential for improvement, severity of heart failure or age.

* * * * *